(12) United States Patent
Eberl et al.

(10) Patent No.: US 7,972,327 B2
(45) Date of Patent: *Jul. 5, 2011

(54) LOW TEMPERATURE LESION FORMATION APPARATUS, SYSTEMS AND METHODS

(75) Inventors: Greg Eberl, Sunnyvale, CA (US); David K. Swanson, Campbell, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 867 days.

This patent is subject to a terminal disclaimer.

(21) Appl. No.: 11/931,180

(22) Filed: Oct. 31, 2007

(65) Prior Publication Data
US 2008/0058791 A1 Mar. 6, 2008

Related U.S. Application Data

(62) Division of application No. 10/842,183, filed on May 10, 2004, now Pat. No. 7,291,142.

(51) Int. Cl.
*A61B 18/02* (2006.01)
(52) U.S. Cl. ............... 606/20; 606/21; 606/22; 606/23
(58) Field of Classification Search ............... 606/20–26
See application file for complete search history.

(56) References Cited

U.S. PATENT DOCUMENTS

| | | |
|---|---|---|
| 3,391,690 A | 7/1968 | Armao |
| 3,924,628 A | 12/1975 | Droegemueller |
| 4,306,561 A | 12/1981 | De Medinaceli |
| 5,147,355 A | 9/1992 | Friedman et al. |
| 5,275,595 A | 1/1994 | Dobak, III |
| 5,423,807 A | 6/1995 | Milder |
| 5,443,463 A | 8/1995 | Stem et al. |
| 5,496,312 A | 3/1996 | Klicek |
| 5,674,218 A | 10/1997 | Rubinsky et al. |
| 5,733,280 A * | 3/1998 | Avitall ............... 606/23 |
| 5,759,182 A | 6/1998 | Varney et al. |
| 5,800,482 A * | 9/1998 | Pomeranz et al. ............ 607/101 |
| 5,868,735 A | 2/1999 | Lafontaine |
| 5,899,898 A | 5/1999 | Arless et al. |
| 5,899,899 A | 5/1999 | Arless et al. |
| 5,902,299 A | 5/1999 | Jayaraman |
| 5,916,213 A | 6/1999 | Haissaguerre et al. |
| 5,957,963 A | 9/1999 | Dobak |
| 5,971,979 A | 10/1999 | Joye et al. |
| 6,048,329 A * | 4/2000 | Thompson et al. ........ 604/95.04 |
| 6,071,274 A | 6/2000 | Thompson et al. |

(Continued)

FOREIGN PATENT DOCUMENTS
WO WO-0180724 11/2001
(Continued)

OTHER PUBLICATIONS

Notice of Allowance dated Jun. 29, 2007 for related U.S. Appl. No. 10/842,180, filed May 10, 2004, Inventor David K. Swanson (6 pages).

(Continued)

*Primary Examiner* — Roy D Gibson
*Assistant Examiner* — Amanda Scott
(74) *Attorney, Agent, or Firm* — Vista IP Law Group LLP

(57) ABSTRACT

Low temperature lesion formation apparatus, systems and methods. The apparatus includes a base member and an inflatable element carried by the base member.

11 Claims, 17 Drawing Sheets

U.S. PATENT DOCUMENTS

| | | | |
|---|---|---|---|
| 6,071,279 A | | 6/2000 | Whayne et al. |
| 6,106,518 A | * | 8/2000 | Wittenberger et al. ......... 606/23 |
| 6,142,994 A | | 11/2000 | Swanson et al. |
| 6,149,677 A | | 11/2000 | Dobak |
| 6,161,543 A | | 12/2000 | Cox et al. |
| 6,164,283 A | | 12/2000 | Lesh |
| 6,217,528 B1 | | 4/2001 | Koblish et al. |
| 6,237,605 B1 | | 5/2001 | Vaska et al. |
| 6,241,722 B1 | | 6/2001 | Dobak et al. |
| 6,245,064 B1 | | 6/2001 | Lesh et al. |
| 6,261,312 B1 | | 7/2001 | Dobak, III |
| 6,270,493 B1 | | 8/2001 | Lalonde et al. |
| 6,290,696 B1 | | 9/2001 | Lafontaine |
| 6,311,692 B1 | | 11/2001 | Vaska et al. |
| 6,314,962 B1 | | 11/2001 | Vaska et al. |
| 6,314,963 B1 | | 11/2001 | Vaska et al. |
| 6,355,029 B1 | | 3/2002 | Joye et al. |
| 6,379,348 B1 | | 4/2002 | Onik |
| 6,416,511 B1 | | 7/2002 | Lesh et al. |
| 6,428,534 B1 | | 8/2002 | Joye et al. |
| 6,451,011 B2 | | 9/2002 | Tu |
| 6,464,700 B1 | | 10/2002 | Koblish et al. |
| 6,475,179 B1 | | 11/2002 | Wang et al. |
| 6,506,189 B1 | | 1/2003 | Rittman, III et al. |
| 6,514,249 B1 | | 2/2003 | Maguire et al. |
| 6,517,536 B2 | | 2/2003 | Hooven et al. |
| 6,527,767 B2 | | 3/2003 | Wang et al. |
| 6,529,756 B1 | | 3/2003 | Phan et al. |
| 6,537,271 B1 | | 3/2003 | Murray et al. |
| 6,542,781 B1 | | 4/2003 | Koblish et al. |
| 6,547,785 B1 | | 4/2003 | Heiner et al. |
| 6,551,309 B1 | | 4/2003 | LePivert |
| 6,565,556 B1 | | 5/2003 | Korpan et al. |
| 6,569,158 B1 | | 5/2003 | Abboud et al. |
| 6,575,933 B1 | | 6/2003 | Wittenberger et al. |
| 6,575,966 B2 | | 6/2003 | Lane et al. |
| 6,602,246 B1 | | 8/2003 | Joye et al. |
| 6,666,858 B2 | * | 12/2003 | Lafontaine ............. 606/21 |
| 6,685,702 B2 | | 2/2004 | Quijano et al. |
| 6,929,639 B2 | * | 8/2005 | Lafontaine ............. 606/20 |
| 6,932,816 B2 | | 8/2005 | Phan |
| 2002/0026182 A1 | | 2/2002 | Joye et al. |
| 2002/0026187 A1 | | 2/2002 | Swanson |
| 2002/0058934 A1 | | 5/2002 | Wang et al. |
| 2002/0068897 A1 | | 6/2002 | Jenkins et al. |
| 2002/0103484 A1 | | 8/2002 | Hooven |
| 2002/0120267 A1 | | 8/2002 | Phan |
| 2002/0151880 A1 | * | 10/2002 | Lafontaine ............. 606/21 |
| 2003/0055416 A1 | | 3/2003 | Damasco et al. |
| 2003/0088240 A1 | | 5/2003 | Saadat |
| 2003/0093068 A1 | | 5/2003 | Hooven |
| 2003/0120267 A1 | | 6/2003 | Kaufman |
| 2003/0158547 A1 | | 8/2003 | Phan |
| 2003/0171742 A1 | | 9/2003 | Mihalik et al. |
| 2004/0044334 A1 | | 3/2004 | LaFontaine |
| 2004/0049181 A1 | | 3/2004 | Stewart et al. |
| 2004/0073203 A1 | | 4/2004 | Yu et al. |
| 2004/0106918 A1 | | 6/2004 | Cox et al. |
| 2004/0199153 A1 | | 10/2004 | Lentz |
| 2005/0010201 A1 | | 1/2005 | Abboud et al. |
| 2005/0027289 A1 | * | 2/2005 | Castellano et al. ......... 606/21 |
| 2005/0119653 A1 | | 6/2005 | Swanson |
| 2005/0251122 A1 | | 11/2005 | Swanson et al. |

FOREIGN PATENT DOCUMENTS

WO    WO-02/38052 A2    5/2002

OTHER PUBLICATIONS

Notice of Allowance dated Jun. 28, 2007,for related U.S. Appl. No. 11/278,699, filed Apr. 5, 2006; Inventor: David K. Swanson (6 pages).

Notice of Allowance dated Mar. 5, 2007,for related U.S. Appl. No. 11/278,699, filed Apr. 5, 2006; Inventor: David K. Swanson (6 pages).

Office Action dated Sep. 18, 2008 for related U.S. Appl. No. 11/931,123, filed Oct. 31, 2007; Inventor: David K. Swanson (4 pages).

Amendment and Response to Office Action dated Dec. 8, 2008, response submitted on Sep. 18, 2008, for related U.S. Appl. No. 11/931,123, filed Oct. 31, 2007; Inventor: David K. Swanson (5 pages).

Office Action dated Jul. 9, 2009 for related U.S. Appl. No. 11/931,123, filed Oct. 31, 2007; Inventor: David K Swanson (11 pages).

Office Action dated May 20, 2010 for related U.S. Appl. No. 11/931,123, filed Oct. 31, 2007; Inventor: David K Swanson (8 pages).

Office Action dated Jun. 14, 2007 for related U.S. Appl. No. 10/842,173, filed May 10, 2004; Inventor: David K. Swanson (7 pages).

Amendment and Response to Office Action dated Oct. 15, 2007, response submitted on Jun. 14, 2007, for related U.S. Appl. No. 10/842,173, filed May 10, 2004; Inventor: David K. Swanson (11 pages).

Office Action dated Feb. 9, 2009, for related U.S. Appl. No. 10/842,173, filed May 10, 2004; Inventor; David K. Swanson (11 pages).

Amendment and Response to Office Action dated Apr. 6, 2009, response submitted on Feb. 9, 2009 , for related U.S. Appl. No. 10/842,173, filed May 10, 2004; Inventor: David K. Swanson (6 pages).

Notice of Allowance dated May 1, 2009 for related U.S. Appl. No. 10/842,173, filed Apr. 10 , 2004; Inventor: David K. Swanson (4 pages).

Office Action dated Feb. 17, 2006 for related U.S. Appl. No. 10/842,173, filed May 10, 2004; Inventor David K. Swanson (15 pages).

Amendment and Response to Office Action dated Feb. 17, 2006, response submitted on Aug. 2, 2006, for related U.S. Appl. No. 10/842,173, filed May 10, 2004; Inventor David K. Swanson (17 pages).

Office Action dated Oct. 11, 2006 for related U.S. Appl. No. 10/842,173, filed May 10, 2004; Inventor David K. Swanson (16 pages).

Amendment and Response to Office Action dated Oct. 11, 2006, response submitted on Jan. 10, 2007, for related U.S. Appl. No. 10/842,173, filed May 10, 2004; Inventor David K. Swanson (17 pages).

Notice of Allowance dated Feb. 13, 2007, for related U.S. Appl. No. 10/842,173, filed May 10, 2004; Inventor David K. Swanson (6 pages).

Office Action dated Jun. 2, 2006 for related U.S. Appl. No. 11/278,694, filed Apr. 5, 2006; Inventor Greg Eberl (7 pages).

Amendment and Response to Office Action dated Jun. 2, 2006, response submitted on Jun. 22, 20066, for related U.S. Appl. No. 11/278,694, filed Apr. 5, 2006; Inventor Greg Eberl (8 pages).

Office Action dated Jul. 21, 2006 for related U.S. Appl. No. 11/278,694, filed Apr. 5, 2006; Inventor Greg Eberl (7 pages).

Amendment and Response to Office Action dated Jul. 21, 2006, response submitted on Aug. 31, 2006, for related U.S. Appl. No. 11/278,694, filed Apr. 5, 2006; Inventor Greg Eberl (10 pages).

Notice of Allowance dated Oct. 20, 2006 for related U.S. Appl. No. 11/278,694, filed Apr. 5, 2006; Inventor Greg Eberl (8 pages).

Office Action dated Feb. 23, 2006 for related U.S. Appl. No. 10/842,180, filed May 10, 2004; Inventor David K. Swanson (7 pages).

Amendment and Response to Office Action dated Feb. 23, 2006, response submitted on Mar. 17, 2006, for related U.S. Appl. No. 10/842,180, filed May 10, 2004; Inventor David K. Swanson (17 pages).

Office Action dated Apr. 12, 2006 for related U.S. Appl. No. 10/842,180, filed May 10, 2004; Inventor David K. Swanson (15 pages).

Amendment and Response to Office Action dated Apr. 12, 2006, response submitted on Aug. 16, 2006, for related U.S. Appl. No. 10/842,180, filed May 10, 2004; Inventor David K. Swanson (15 pages).

Office Action dated Nov. 9, 2006 for related U.S. Appl. No. 10/842,180, filed May 10, 2004; Inventor David K. Swanson (15 pages).

RCE, Amendment and Response to Office Action dated Nov. 9, 2006, response submitted on Feb. 8, 2007, for related U.S. Appl. No. 10/842,180, filed May 10, 2004; Inventor David K. Swanson (12 pages).

Office Action dated Mar. 1, 2007 for related U.S. Appl. No. 10/842,180, filed May 10, 2004; Inventor David K. Swanson (14 pages).

Amendment and Response to Office Action dated Mar. 1, 2007, response submitted on Apr. 27, 2007, for related U.S. Appl. No. 10/842,180, filed May 10, 2004; Inventor David K. Swanson (13 pages).

Office Action dated Jun. 2, 2006 for related U.S. Appl. No. 11/278,699, filed Apr. 5, 2006; Inventor David K. Swanson (12 pages).

Amendment and Response to Office Action dated Jun. 2, 2006, response submitted on Jun. 22, 2006, for related U.S. Appl. No. 11/278,699, filed Apr. 5, 2006; Inventor David K. Swanson (13 pages).

Office Action dated Jul. 21, 2006 for related U.S. Appl. No. 11/278,699, filed Apr. 5, 2006; Inventor David K. Swanson (12 pages).

Amendment and Response to Office Action dated Jul. 21, 2006, response submitted on Oct. 28, 2006, for related U.S. Appl. No. 11/278,699, filed Apr. 5, 2006; Inventor David K. Swanson (13 pages).

Office Action dated Dec. 19, 2006 for related U.S. Appl. No. 11/278,699, filed Apr. 5, 2006; Inventor David K. Swanson (10 pages).

Amendment and Response to Office Action dated Dec. 19, 2006, response submitted on Feb. 14, 2007, for related U.S. Appl. No. 11/278,699, filed Apr. 5, 2006; Inventor David K. Swanson (6 pages).

Notice of Allowance dated Jun. 5, 2007, for related U.S. Appl. No. 11/278,699, filed Apr. 5, 2006; Inventor David K. Swanson (7 pages).

RCE dated Jun. 5, 2007 submitted for related U.S. Appl. No. 11/278,699, filed Apr. 5, 2006; Inventor David K. Swanson (2 pages).

* cited by examiner

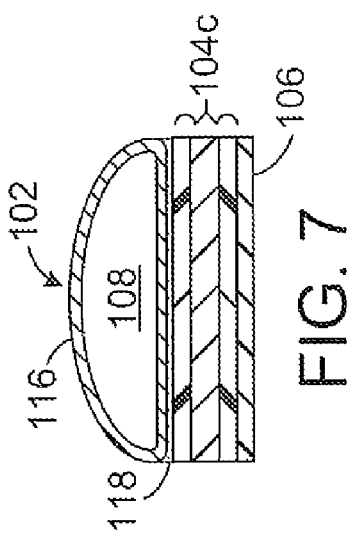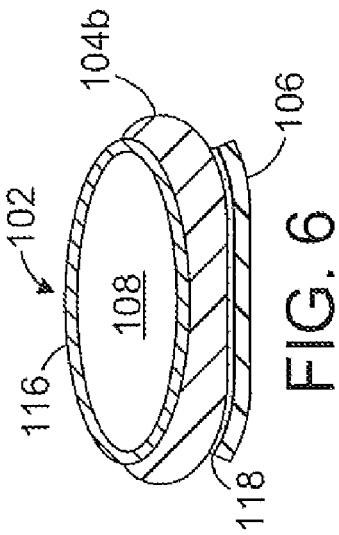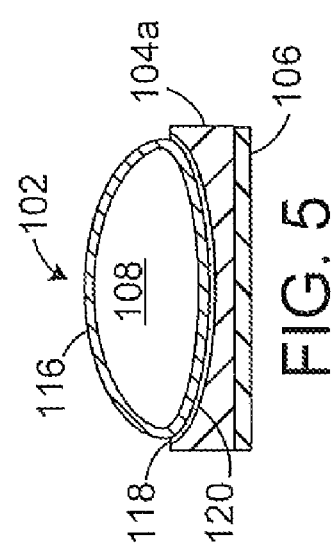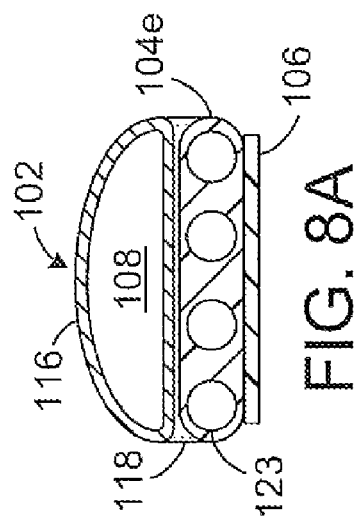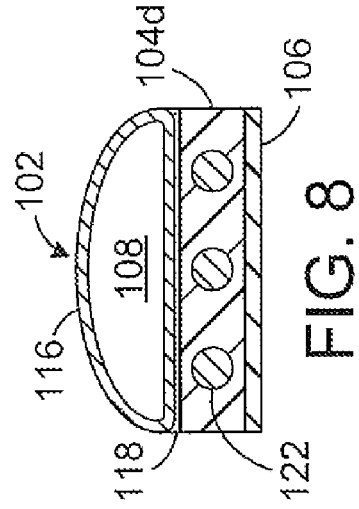

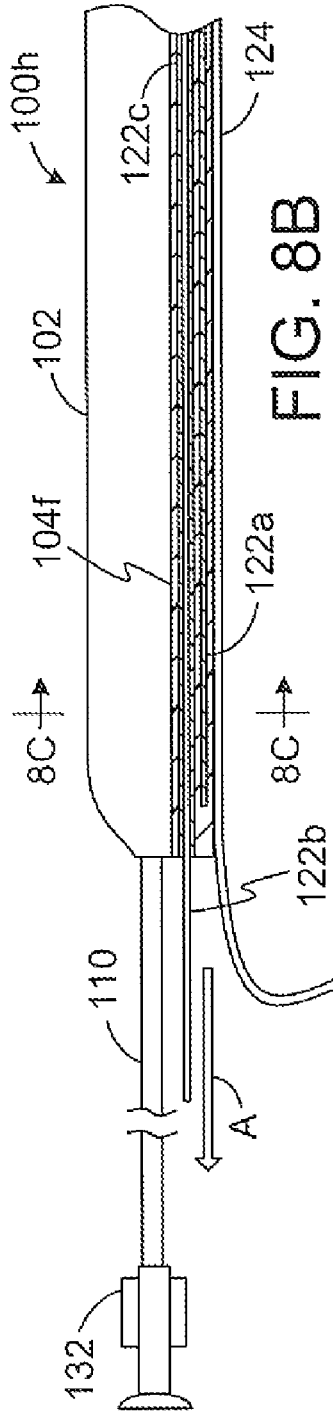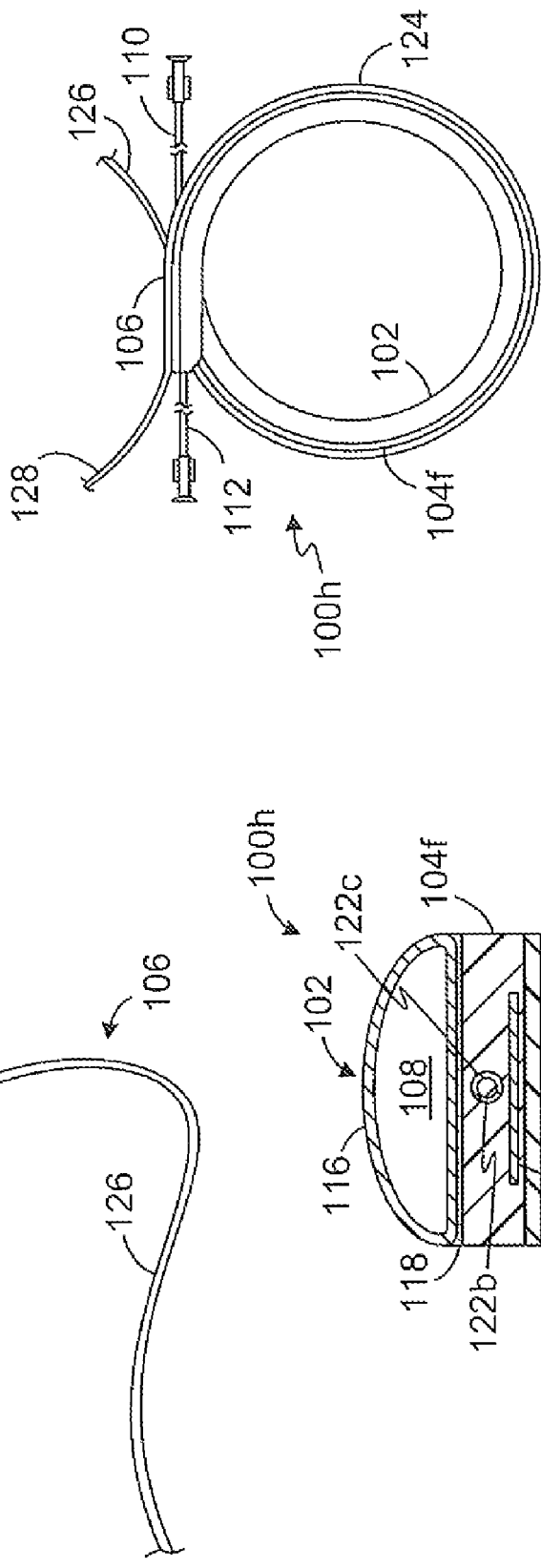

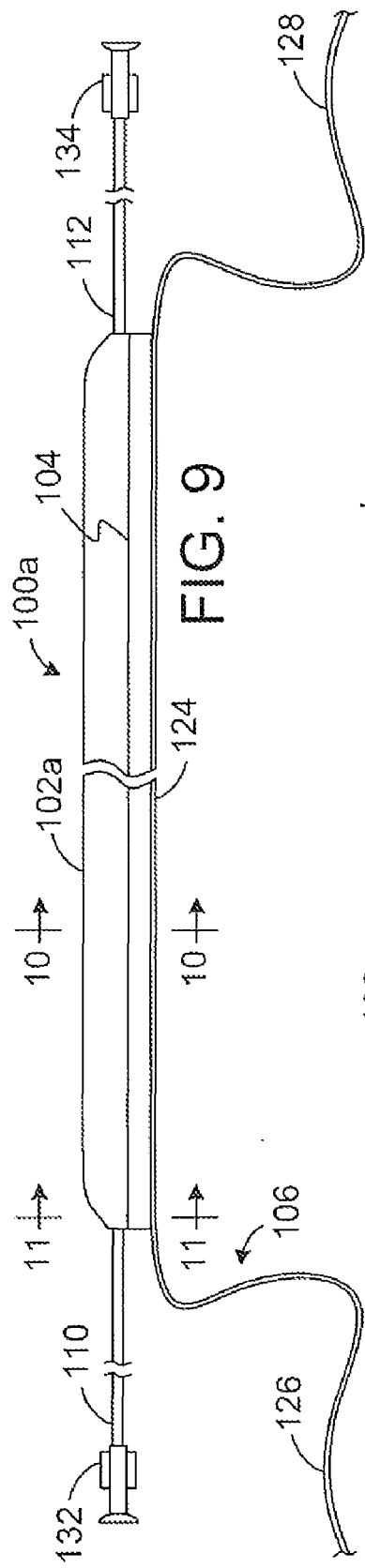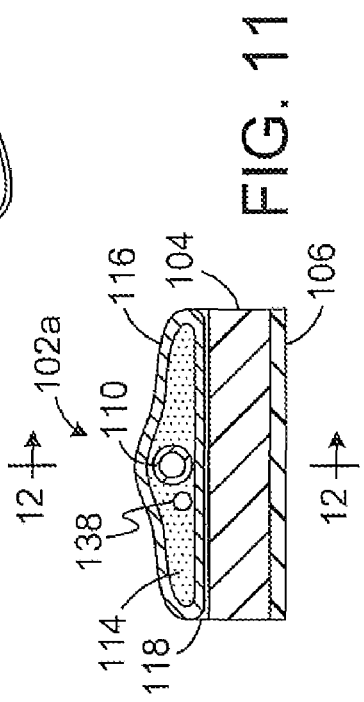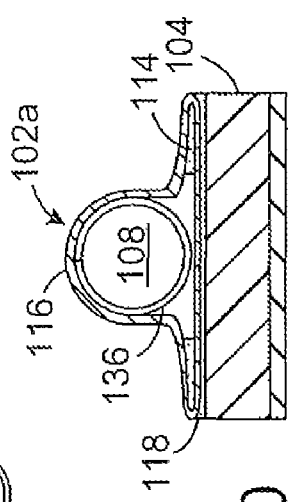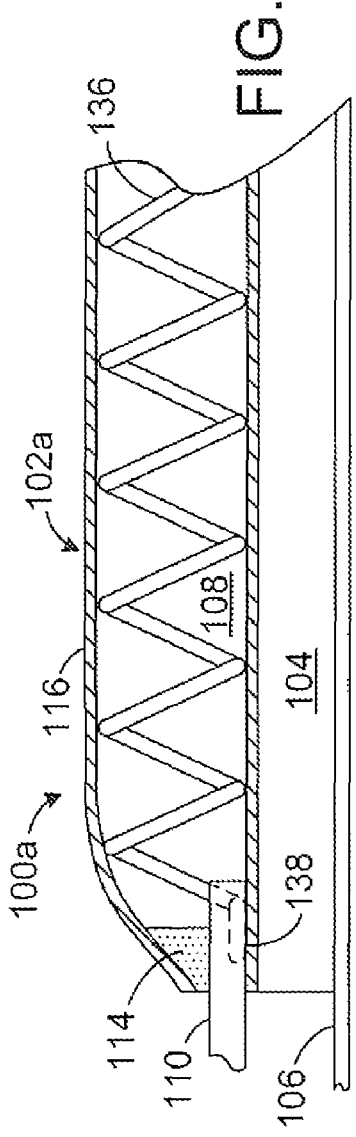

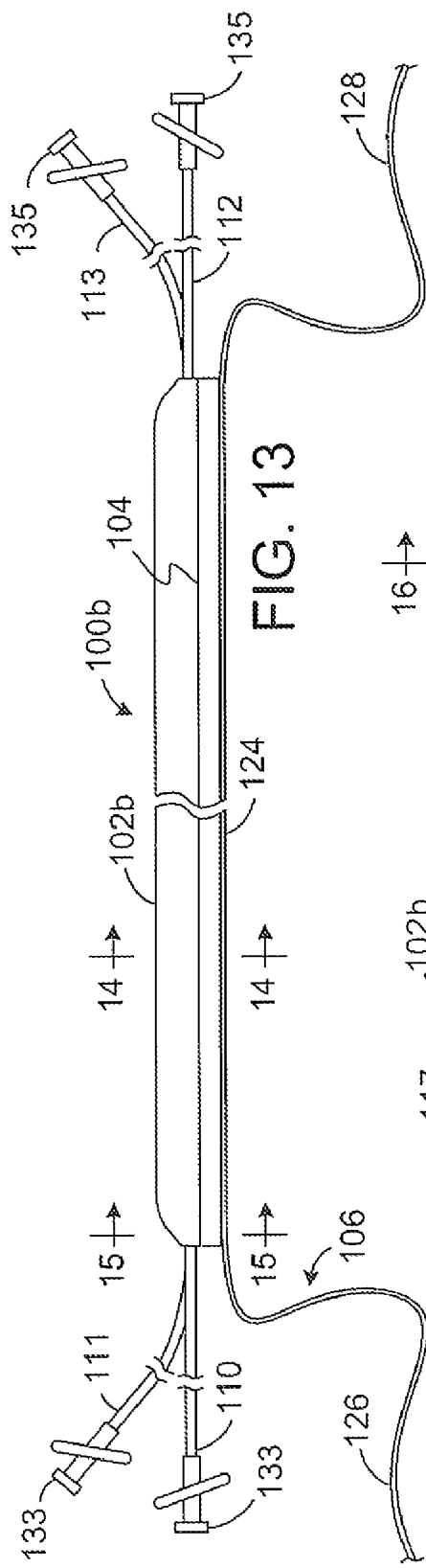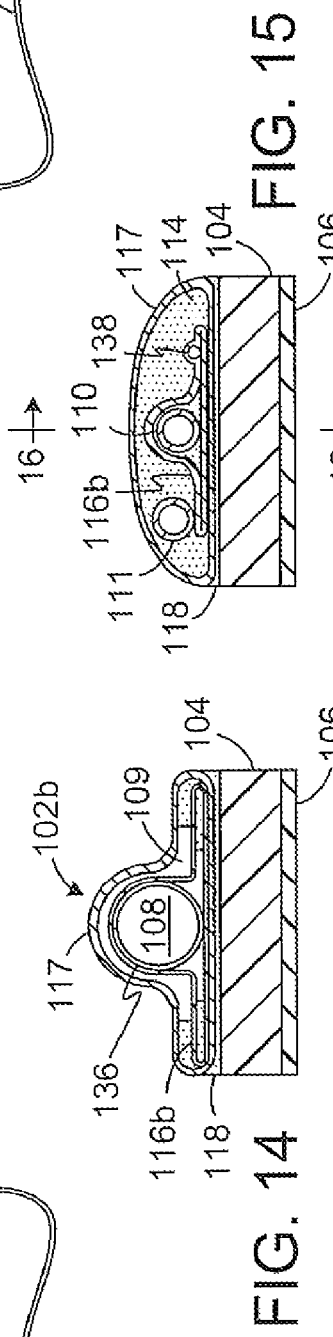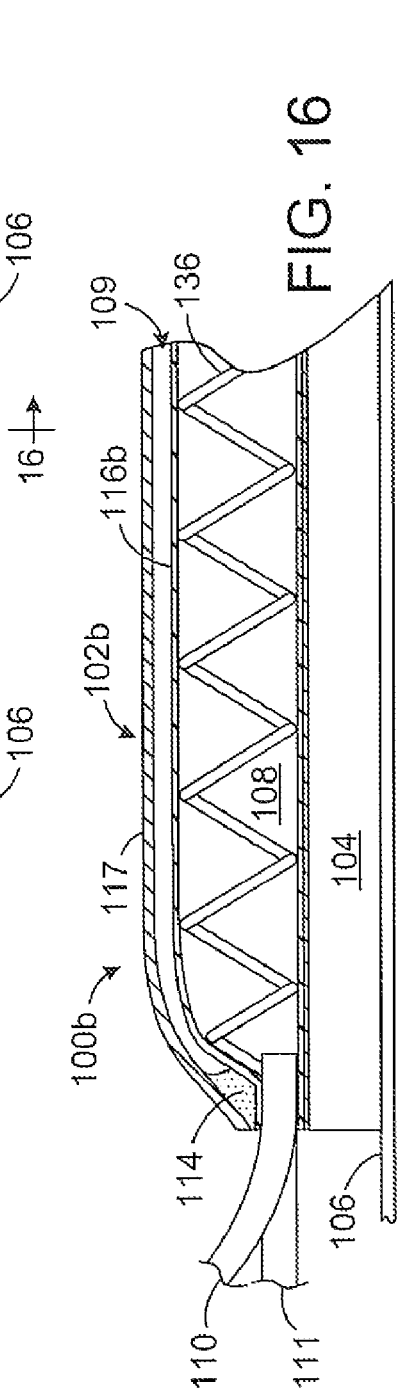

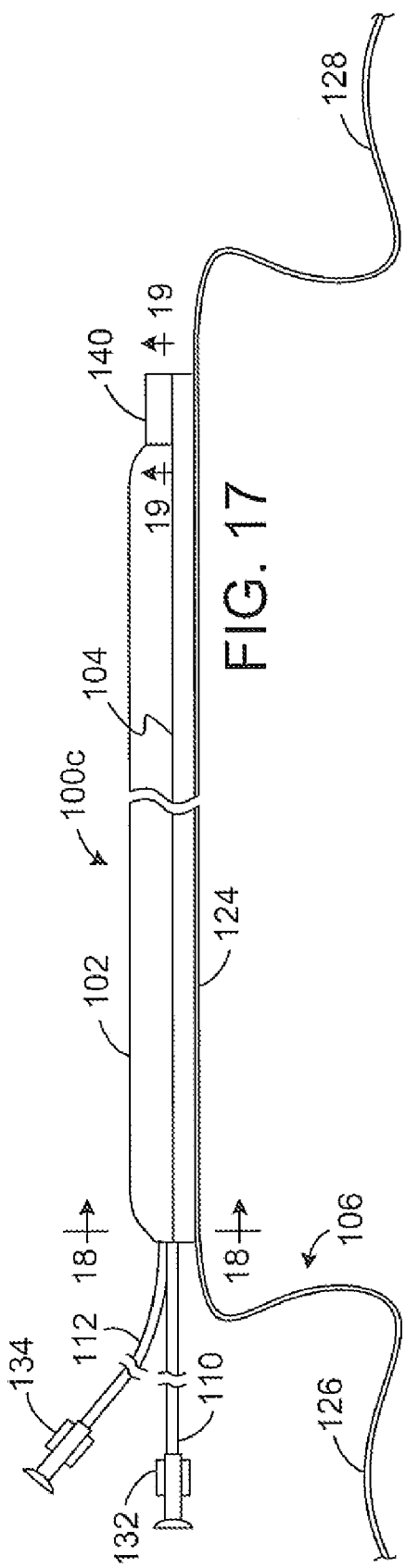
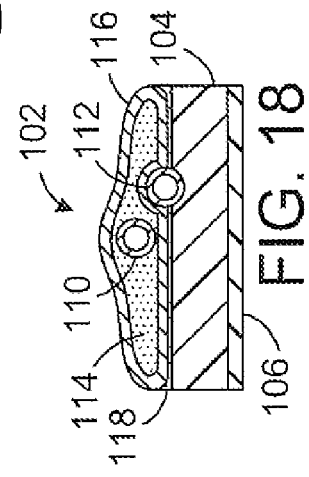
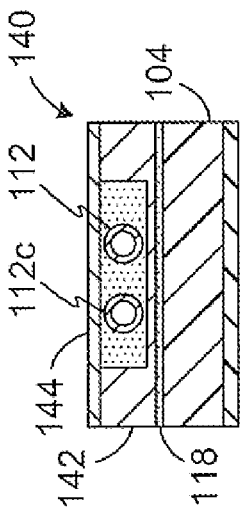

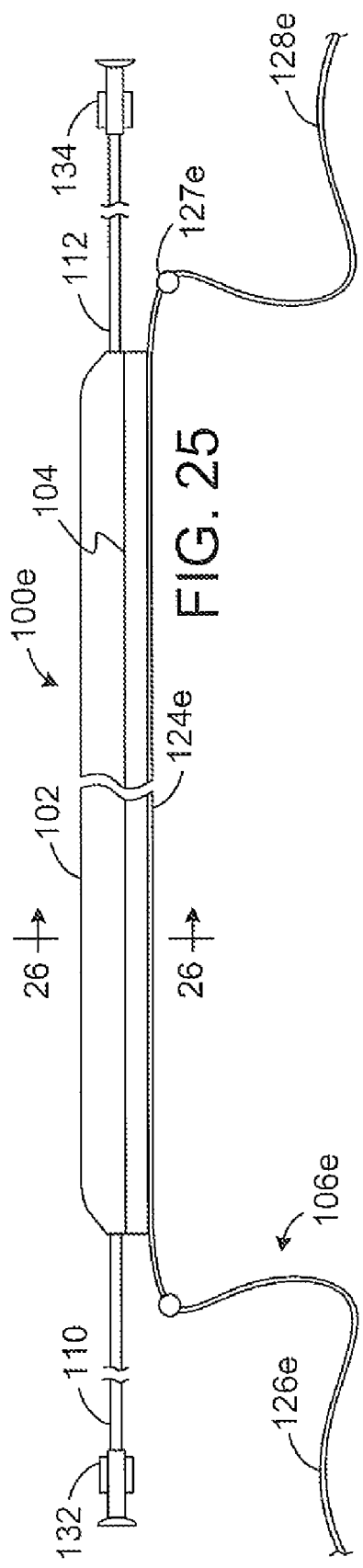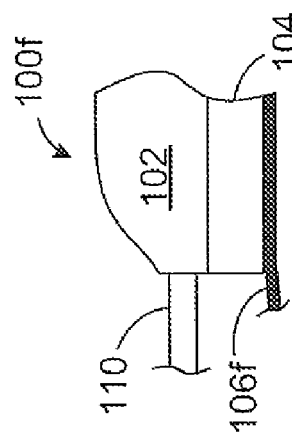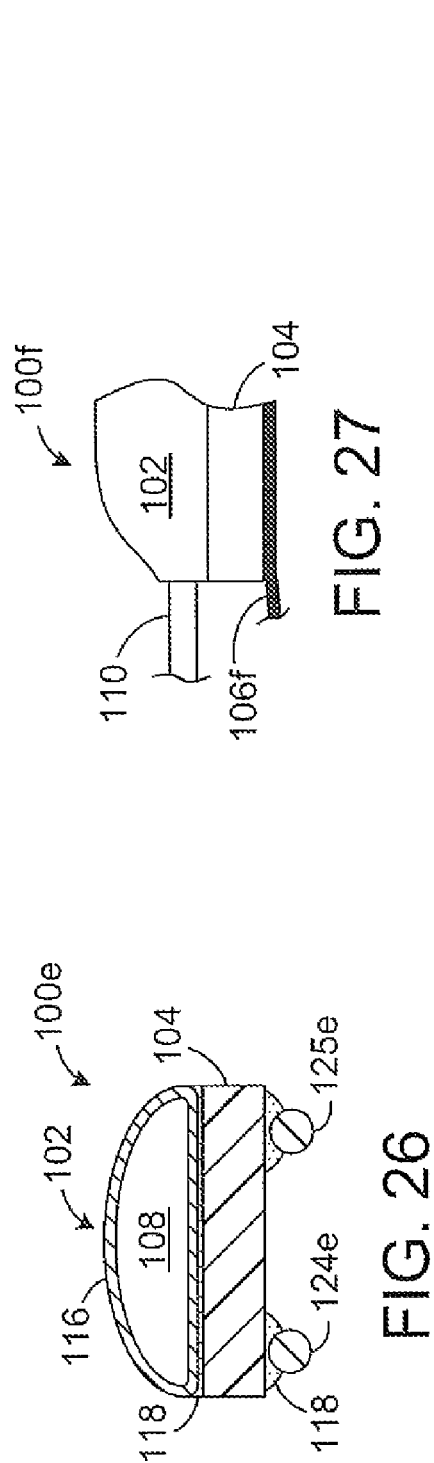

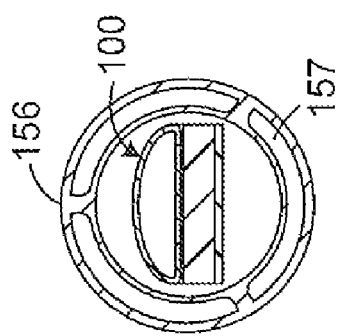
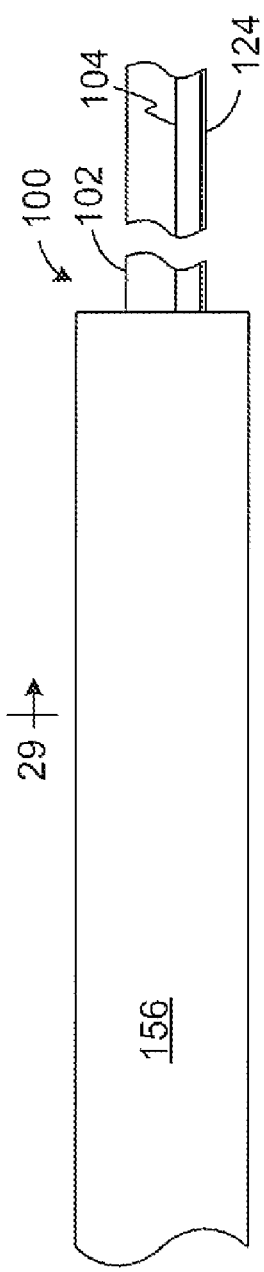
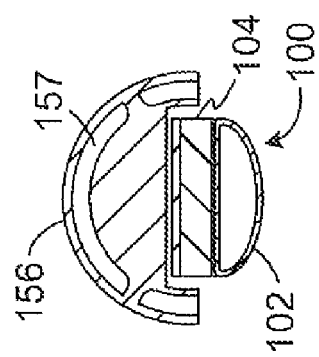
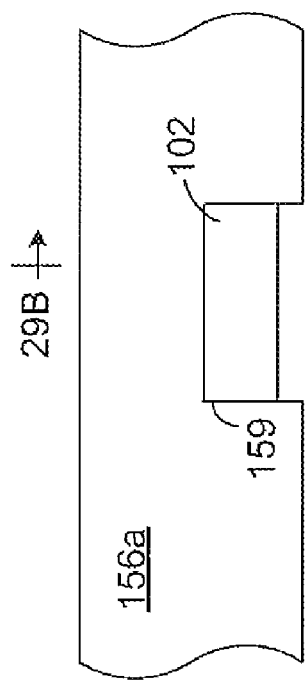

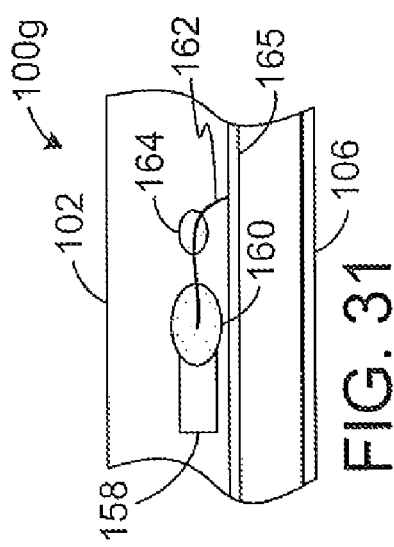
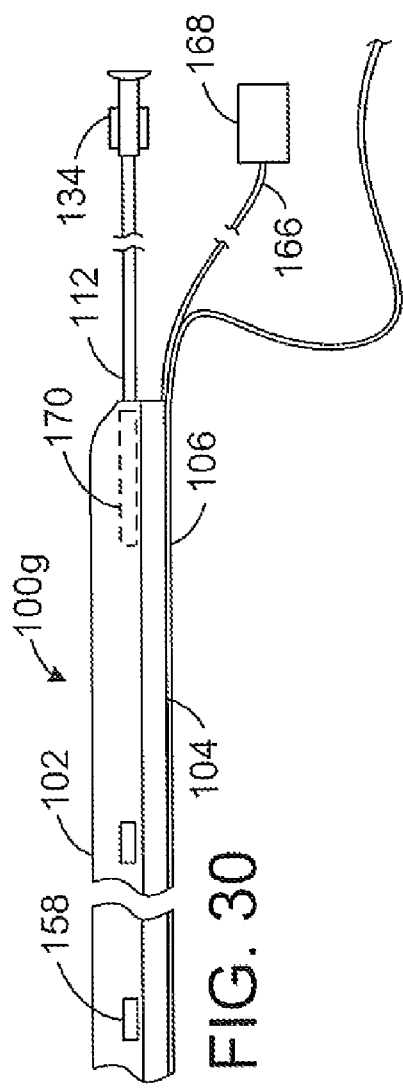
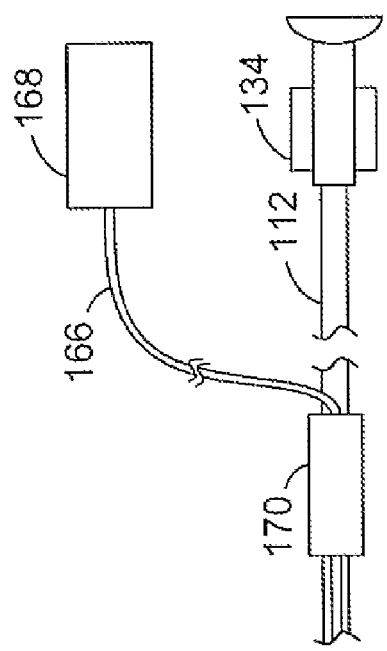

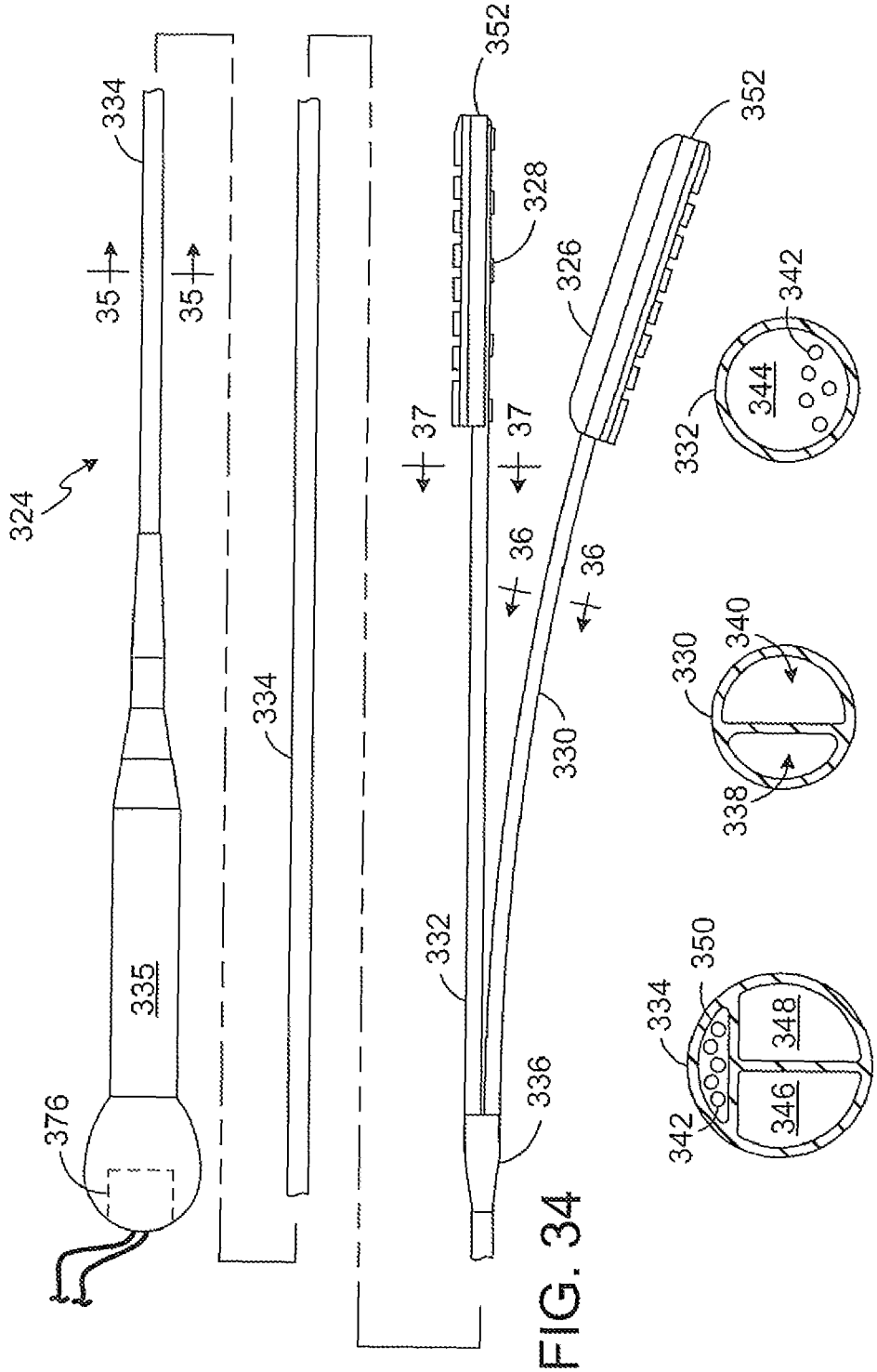

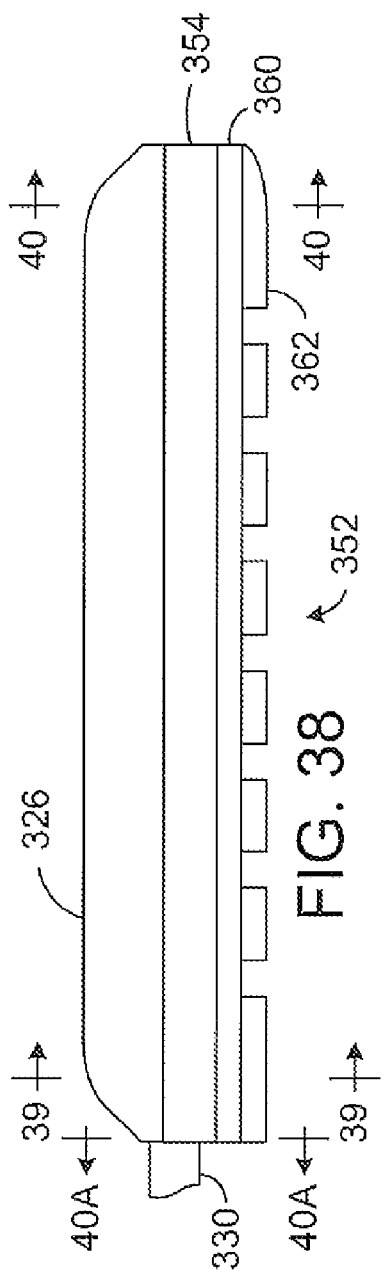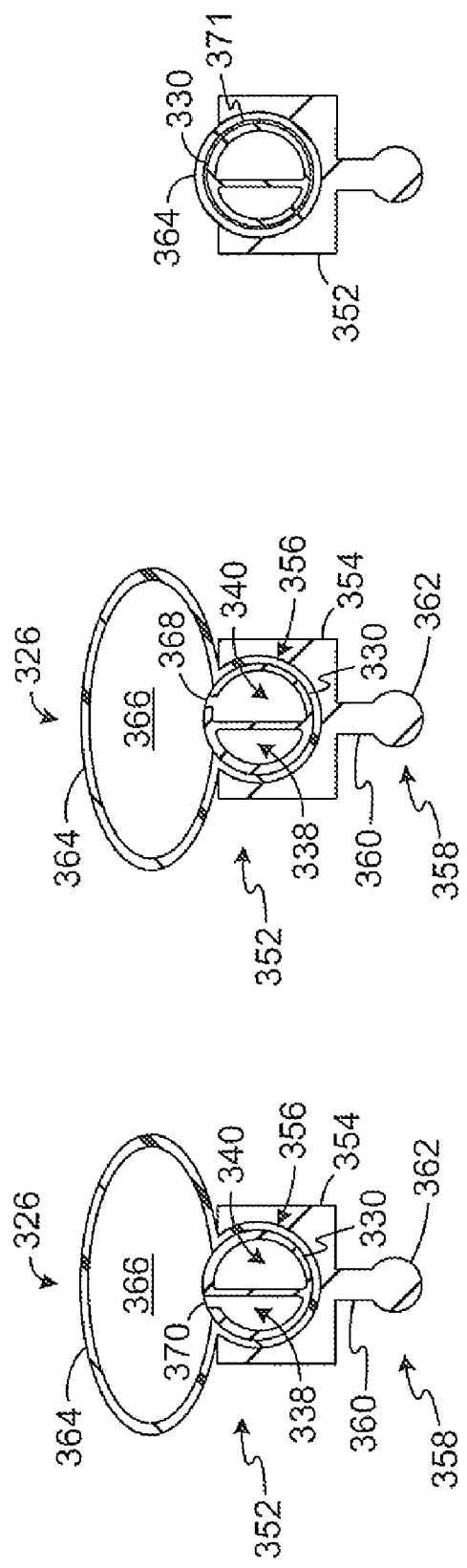

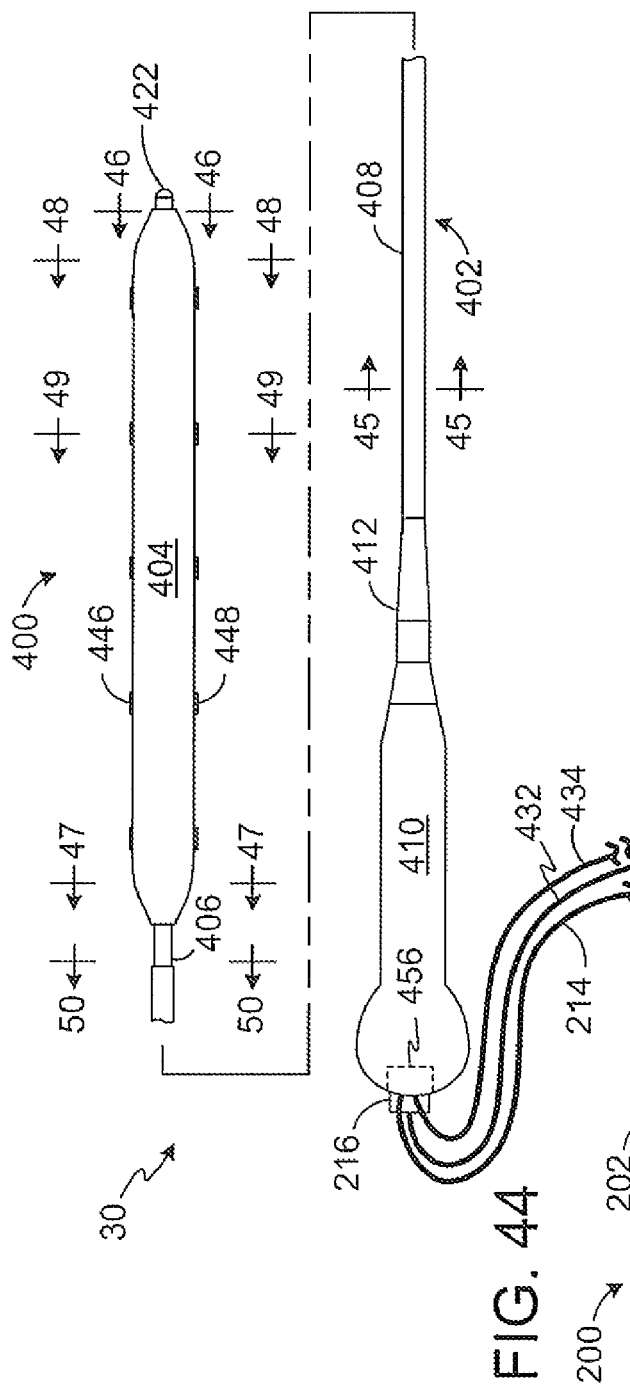
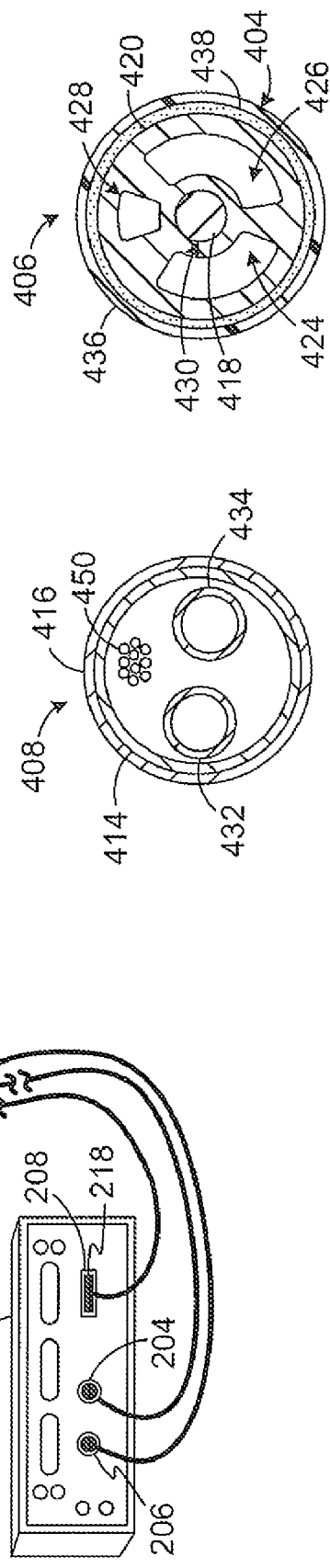

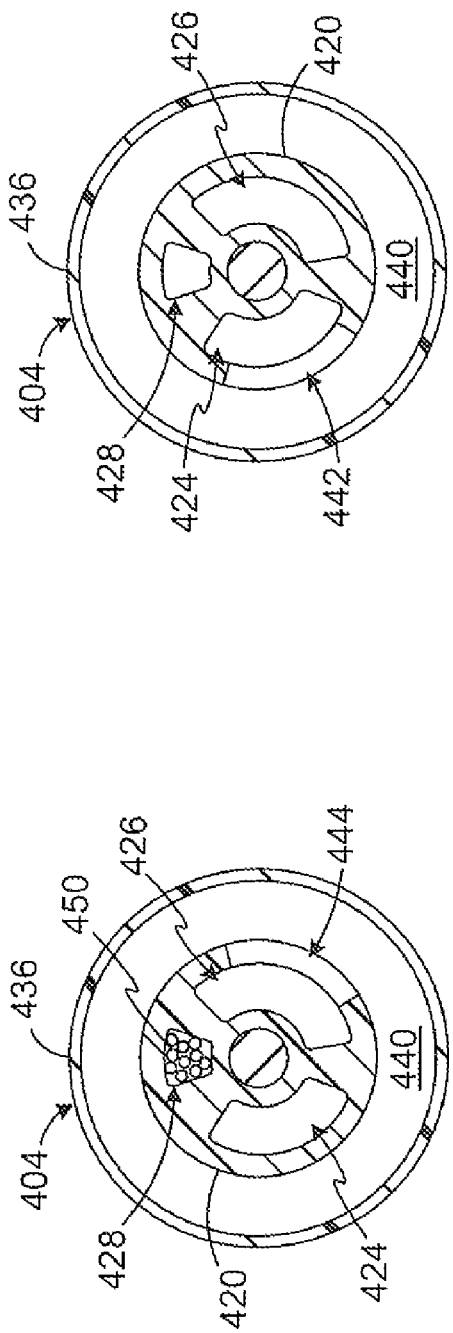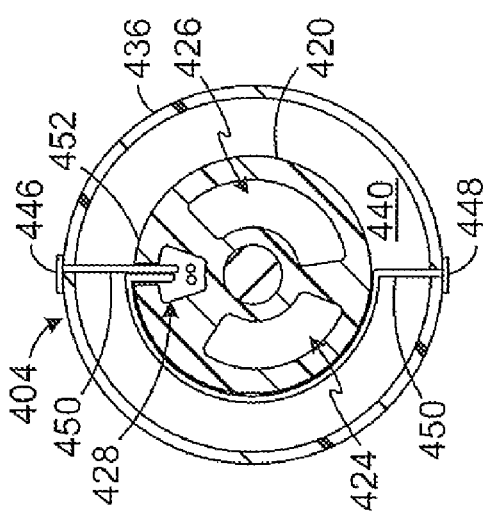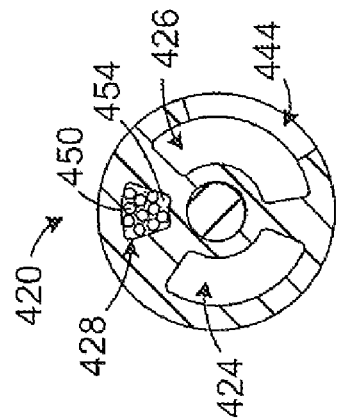

LOW TEMPERATURE LESION FORMATION APPARATUS, SYSTEMS AND METHODS

CROSS-REFERENCE TO RELATED APPLICATION

This application is a divisional application of U.S. patent application Ser. No. 10/842,183, filed May 10, 2004, now U.S. Pat. No. 7,291,142, the priority of which is claimed under 35 U.S.C. §120, and the contents of which are incorporated herein by reference as though set forth in full.

BACKGROUND OF THE INVENTIONS

1. Field of Inventions

The present inventions relate generally to devices for performing therapeutic operations on body tissue.

2. Description of the Related Art

There are many instances where therapeutic elements must be positioned adjacent to body tissue. One instance involves the formation of therapeutic lesions to the treat cardiac conditions such as atrial fibrillation, atrial flutter and arrhythmia. Therapeutic lesions, which may also be used to treat conditions in other regions of the body such as the prostate, liver, brain, gall bladder, uterus, breasts, lungs and other solid organs, are typically formed by ablating tissue.

Cryogenic cooling devices are one example of the devices that have been used to form lesions in tissue. During the cryo-ablation of soft tissue (i.e. tissue other than blood, bone and connective tissue), ice crystals disrupt cell and organelle membranes and it is the disruption that kills the tissue. A cryogenic element, such as a balloon or hollow metal tip, is carried on the distal end of a catheter or surgical probe (referred to herein collectively as "probes"), placed in contact with tissue and cooled to a temperature that will cause tissue death. The cryogenic element may be cooled by a variety of techniques. One technique employs the Joule-Thompson ("JT") effect. Here, cryogenic cooling occurs as a result of a rapid decrease of gas pressure that occurs within the therapeutic element. Pressurized cryogenic fluid, such as liquid nitrous oxide, is directed into the therapeutic element where it undergoes rapid phase change and a rapid expansion of the gas from a high-pressure to a lower pressure state. The reaction is endothermic and produces temperatures as low as minus 70.degree. C. at the therapeutic element. In some instances, the cryogenic fluid is pre-cooled in order to increase the cooling power delivered to the targeted tissue. The cryogenic element may also be cooled by directing supercooled fluid through the catheter or surgical probe to the cryogenic element. Here, the temperature at the therapeutic element can be as low as minus 100.degree. C. when it enters the patient.

The present inventors have determined that conventional cryogenic cooling devices are susceptible to improvement. For example, the present inventors have determined that conventional cryogenic cooling devices can damage non-target tissue near the tissue in which the therapeutic lesions are being formed. The present inventors have also determined that it can be difficult to achieve good tissue contact with conventional cryogenic devices because they are relatively turgid. Some conventional cryogenic cooling devices are susceptible to leaks, which can result in the release of toxic chemicals (e.g. perfluorocarbons) into the patient's blood stream during endocardial procedures. Additionally, the inventors herein have determined that the manner in which temperature is monitored during cryogenic lesion formation procedures.

SUMMARY OF THE INVENTIONS

An apparatus in accordance with one invention herein includes a base member, an inflatable cryogenic element carried by the base member and a connector, associated with at least one of the base member and the inflatable cryogenic element, adapted to maintain the inflatable cryogenic element in the looped orientation. A system in accordance with one invention herein includes such an apparatus and a source of cryogenic fluid. A method in accordance with one invention herein includes the steps of positioning an apparatus including an inflatable cryogenic element in a looped orientation around a tissue structure, securing at least two portions of the apparatus relative to one another to maintain the looped orientation and directing cryogenic fluid through the inflatable cryogenic element.

An apparatus in accordance with one invention herein includes an inflatable cryogenic element and a base member that carries the inflatable cryogenic element, is pre-shaped into a loop configuration, and is bendable into a non-loop configuration. A system in accordance with one invention herein includes such an apparatus and a source of cryogenic fluid. A method in accordance with one invention herein includes the steps of bending an apparatus including an inflatable cryogenic element into a looped orientation around a tissue structure with a pre-shaped portion of the apparatus, maintaining the apparatus in the looped orientation and directing cryogenic fluid through the inflatable cryogenic element.

An apparatus in accordance with one invention herein includes an inflatable cryogenic apparatus configured to be removably secured to a first clamp member and a temperature sensor apparatus configured to be removably secured to a second clamp member. A clamp in accordance with one invention herein includes first and second clamp members, an inflatable cryogenic apparatus carried by the first clamp member, and a temperature sensor apparatus carried by the second clamp member. Systems in accordance with inventions herein include a source of cryogenic fluid and the apparatus or the clamp. A method in accordance with one invention herein includes the steps supplying cryogenic fluid to a cryogenic apparatus on the first opposing surface and measuring temperature on the second opposing surface.

An apparatus in accordance with one invention herein includes a base member configured to be removably secured to a clamp member and an inflatable cryogenic element, carried by the base member, defining a longitudinal axis and a non-circular inflated shape in a cross-section perpendicular to the longitudinal axis. A clamp in accordance with one invention herein includes a cryogenic apparatus including an inflatable cryogenic element defining a longitudinal axis and a non-circular inflated shape in a cross-section perpendicular to the longitudinal axis.

A method in accordance with one invention herein includes the steps of positioning a resilient inflatable cryogenic element adjacent to tissue, inflating the resilient inflatable cryogenic element with cryogenic fluid and maintaining pressure within the resilient inflatable cryogenic element below about 100 mm Hg. A system in accordance with one invention herein includes a source of cryogenic fluid and resilient inflatable cryogenic element adapted to be operably connected to the source of cryogenic fluid. The pressure within the resilient inflatable cryogenic element is maintained below about 100 mm Hg when the source of cryogenic fluid supplies the cryogenic fluid to the resilient inflatable cryogenic element.

An apparatus in accordance with one invention herein includes a resilient inflatable cryogenic apparatus configured to be removably secured to a clamp member and to operate at a maximum internal pressure of about 100 mm Hg. A clamp in accordance with one invention herein includes a resilient inflatable cryogenic apparatus configured to operate at a maximum internal pressure of about 100 mm Hg.

A surgical probe in accordance with one invention herein includes a relatively short shaft, an inflatable cryogenic element defining an exterior surface, and at least one temperature sensor on the exterior of the inflatable cryogenic element.

A method in accordance with one invention herein includes the steps of positioning an inflatable cryogenic element on the tissue structure with a temperature sensor between a portion of the inflatable cryogenic element and a portion of the tissue surface, supplying cryogenic fluid to the inflatable cryogenic element, and measuring tissue temperature with the temperature sensor.

A surgical probe in accordance with one invention herein includes a relatively short shaft and a resilient inflatable cryogenic element, carried by the relatively short shaft, and configured to operate at a maximum internal pressure of about 100 mm Hg. A system in accordance with one invention herein includes such a surgical probe. A method in accordance with one invention herein includes the steps of positioning a resilient inflatable cryogenic element on the tissue structure with a surgical probe, inflating the resilient inflatable cryogenic element with cryogenic fluid and maintaining pressure within the resilient inflatable cryogenic element below about 100 mm Hg.

There is a wide variety of advantages associated with the present inventions. By way of example, but not limitation, and as described in detail below, at least some of the present inventions prevent damage to non-target tissue near the tissue in which the therapeutic lesions are being formed. As described in detail below, at least some of the present inventions achieve superior tissue contact because they are relatively resilient. As described in detail below, at least some of the present inventions are especially useful in applications outside the blood stream (such as epicardial applications) where leaks are less likely to harm the patient. As described in detail below, because at least some of the present inventions are configured to operate at relatively low pressure, the volume of cryogenic fluid that is lost in the unlikely event of a leak will be lower than conventional devices which operate at high pressure. As described in detail below, at least some of the present inventions provide superior temperature monitoring capabilities.

BRIEF DESCRIPTION OF THE DRAWINGS

Detailed description of preferred embodiments of the inventions will be made with reference to the accompanying drawings.

FIG. 5 is a section view of a lesion formation apparatus in accordance with a preferred embodiment of a present invention.

FIG. 6 is a section view of a lesion formation apparatus in accordance with a preferred embodiment of a present invention.

FIG. 7 is a section view of a lesion formation apparatus in accordance with a preferred embodiment of a present invention.

FIG. 8 is a section view of a lesion formation apparatus in accordance with a preferred embodiment of a present invention.

FIG. 8A is a section view of a lesion formation apparatus in accordance with a preferred embodiment of a present invention.

FIG. 8B is a partial side view of a lesion formation apparatus in accordance with a preferred embodiment of a present invention.

FIG. 8C is a partial section view taken along line 8C-8C in FIG. 8B.

FIG. 8D is a side view of the lesion formation apparatus illustrated in FIG. 8B in a loop orientation.

FIG. 9 is a side view of a lesion formation apparatus in accordance with a preferred embodiment of a present invention.

FIG. 10 is a section view taken along line 10-10 in FIG. 9.

FIG. 11 is a section view taken along line 11-11 in FIG. 9.

FIG. 12 is a partial section view taken along line 12-12 in FIG. 11.

FIG. 13 is a side view of a lesion formation apparatus in accordance with a preferred embodiment of a present invention.

FIG. 14 is a section view taken along line 14-14 in FIG. 13.

FIG. 15 is a section view taken along line 15-15 in FIG. 13.

FIG. 16 is a partial section view taken along line 16-16 in FIG. 15.

FIG. 17 is a side view of a lesion formation apparatus in accordance with a preferred embodiment of a present invention.

FIG. 18 is a section view taken along line 18-18 in FIG. 17.

FIG. 19 is a partial section view taken along line 19-19 in FIG. 17.

FIG. 20 is a section view taken along line 20-20 in FIG. 19.

FIG. 25 is a side view of a lesion formation apparatus in accordance with a preferred embodiment of a present invention.

FIG. 26 is a section view taken along line 26-26 in FIG. 25.

FIG. 27 is a side view of a portion of a lesion formation apparatus in accordance with a preferred embodiment of a present invention.

FIG. 28 is a side view of a portion of a lesion formation apparatus in accordance with a preferred embodiment of a present invention.

FIG. 29 is a section view taken along line 29-29 in FIG. 28.

FIG. 29A is a side view of a portion of a lesion formation apparatus in accordance with a preferred embodiment of a present invention.

FIG. 29B is a section view taken along line 29B-29B in FIG. 29A.

FIG. 30 is a side view of a portion of a lesion formation apparatus in accordance with a preferred embodiment of a present invention.

FIG. 31 is a side view of a portion of the lesion formation apparatus illustrated in FIG. 30.

FIG. 32 is a side view of a portion of a lesion formation apparatus in accordance with a preferred embodiment of a present invention.

FIG. 34 is a plan view of a tissue coagulation assembly in accordance with a preferred embodiment of a present invention.

FIG. 35 is a section view taken along line 35-35 in FIG. 34.
FIG. 36 is a section view taken along line 36-36 in FIG. 34.
FIG. 37 is a section view taken along line 37-37 in FIG. 34.
FIG. 38 is an enlarged view of a portion of the tissue coagulation assembly illustrated in FIG. 34.
FIG. 39 is a section view taken along line 39-39 in FIG. 38.
FIG. 40 is a section view taken along line 40-40 in FIG. 38.
FIG. 40A is a section view taken along line 40A-40A in FIG. 38.
FIG. 44 is a perspective view of a surgical system in accordance with a preferred embodiment of a present invention.
FIG. 45 is a section view taken along line 45-45 in FIG. 44.
FIG. 46 is a section view taken along line 46-46 in FIG. 44.
FIG. 47 is a section view taken along line 47-47 in FIG. 44.
FIG. 48 is a section view taken along line 48-48 in FIG. 44.
FIG. 49 is a section view taken along line 49-49 in FIG. 44.
FIG. 50 is a section view taken along line 50-50 in FIG. 44.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:
  Introduction
  Exemplary Lesion Formation Apparatus Capable of Being Secured Around an Organ
  Exemplary Clamp Based Lesion Formation Apparatus
  Exemplary Probe Based Lesion Formation Apparatus The section titles and overall organization of the present detailed description are for the purpose of convenience only and are not intended to limit the present inventions.

Introduction

This specification discloses a number of structures, mainly in the context of cardiac treatment, because the structures are well suited for use with myocardial tissue. Nevertheless, it should be appreciated that the structures are applicable for use in therapies involving other types of soft tissue. For example, various aspects of the present inventions have applications in procedures concerning other regions of the body such as the prostate, liver, brain, gall bladder, uterus, breasts, lungs, and other solid organs.

Figure 1:
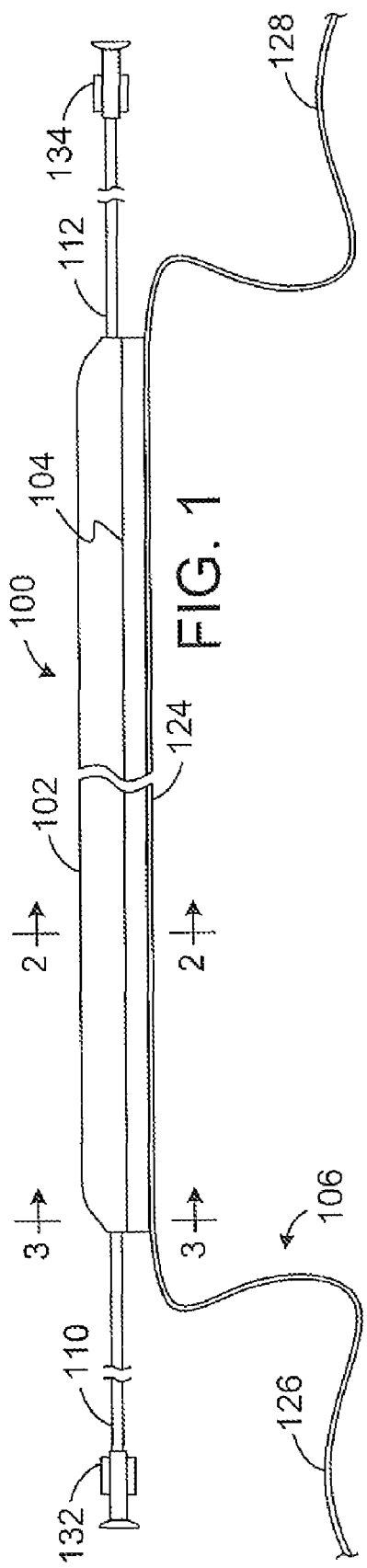
FIG. 1 is a side view of a lesion formation apparatus in accordance with a preferred embodiment of a present invention.
Figure 3:
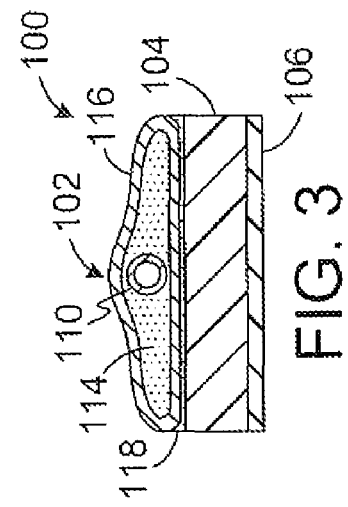
FIG. 3 is a section view taken along line 3-3 in FIG. 1.
Figure 2:
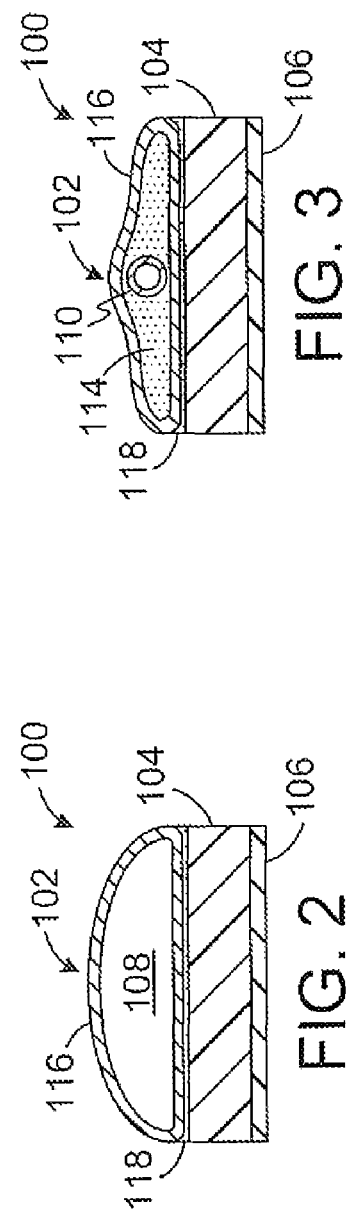
FIG. 2 is a section view taken along line 2-2 in FIG. 1.

II. Exemplary Lesion Formation Apparatus Capable of Being Secured Around an Organ A lesion formation apparatus 100 in accordance with a preferred embodiment of a present invention is illustrated in FIGS. 1-3. The illustrated embodiment includes an inflatable cryogenic element 102 carried on a base member 104 and a connector device 106 that may be used to position the longitudinal ends of the inflatable cryogenic element adjacent to one another. A fluid transmission space 108 is defined within the inflatable cryogenic element 102. The exemplary lesion formation apparatus 100 also includes an infusion lumen 110 and a ventilation lumen 112 that extend a short distance into the longitudinal ends of the inflatable cryogenic element 102. The infusion and ventilation lumens 110 and 112, which are in communication with the fluid transmission space 108, are held in place with adhesive material 114. The adhesive material 114 also seals the longitudinal ends of the inflatable cryogenic element 102. Each of these elements is discussed in greater detail below.

Figure 4:
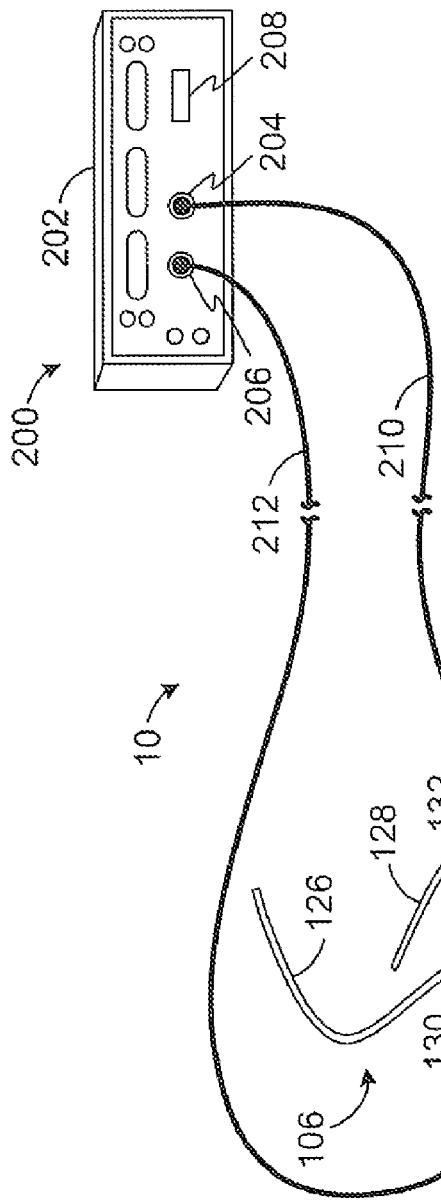
FIG. 4 is a perspective view showing a surgical system including the lesion formation apparatus illustrated in FIG. 1.

As illustrated for example in FIG. 4, the lesion formation apparatus 100 is connected to a cryogenic fluid supply and control apparatus 200 in a surgical system 10. The cryogenic fluid supply and control apparatus 200, which may be used in combination with any of the other lesion formation apparatus described herein, includes housing 202, a fluid outlet port 204, a fluid inlet port 206 and an electrical connector 208. The fluid outlet port 204 may be coupled to the infusion lumen 110 by a tube 210, and the fluid inlet port 206 may be coupled to the ventilation lumen 112 by a tube 212. As discussed below with reference to FIGS. 30-32, the electrical connector 208 may be used to connect the cryogenic fluid supply and control apparatus 200 to, for example, a connector that is associated with temperature sensors and/or a valve, in those instances where the apparatus includes the temperature sensors and/or a valve.

Figure 4A:
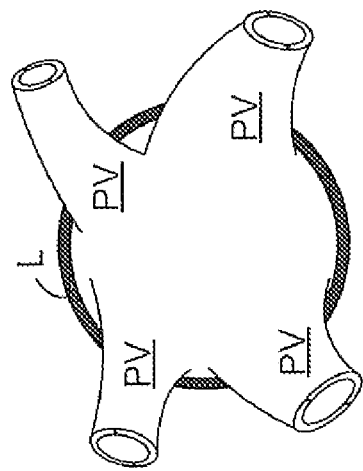
FIG. 4A is perspective view showing a continuous lesion formed around the pulmonary veins.
Figure 21:
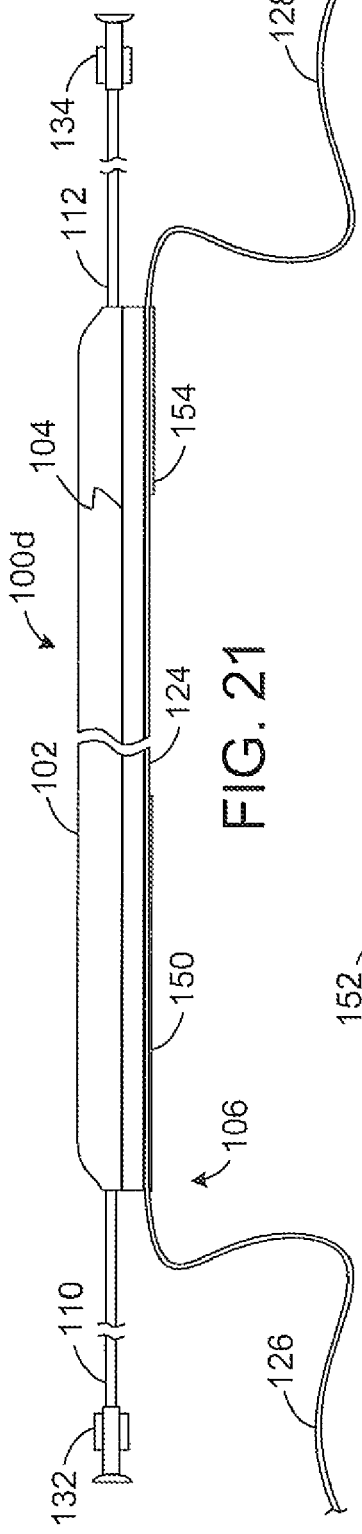
FIG. 21 is a side view of a lesion formation apparatus in accordance with a preferred embodiment of a present invention.
Figure 22:
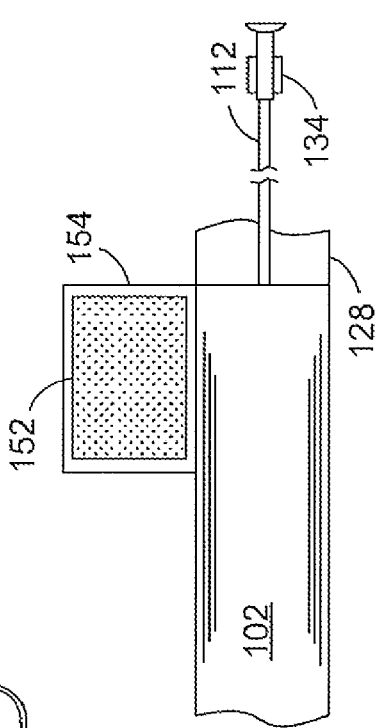
FIG. 22 is a top view of a portion of the lesion formation apparatus illustrated in FIG. 21.
Figure 23:
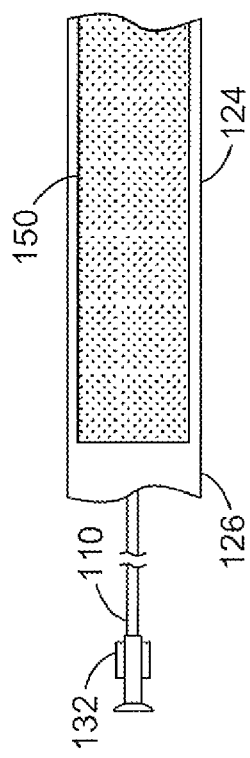
FIG. 23 is a bottom view of a portion of the lesion formation apparatus illustrated in FIG. 21.
Figure 24:
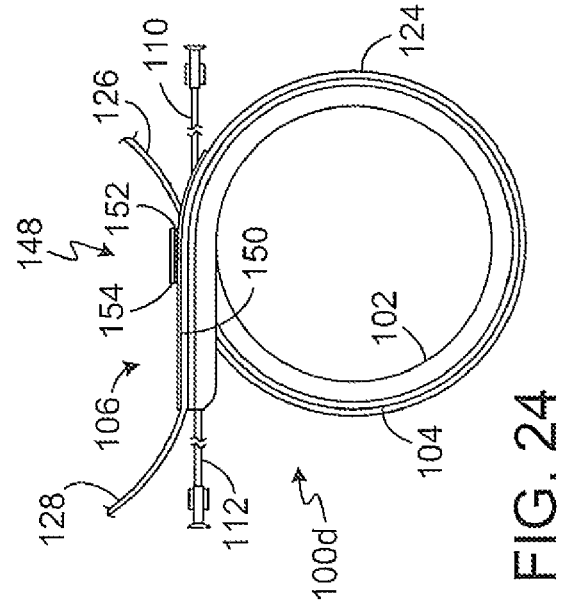
FIG. 24 is a side view of the lesion formation apparatus illustrated in FIG. 21 in a looped orientation.

The lesion formation apparatus 100 may be positioned around portions of organs during lesion formation procedures performed with the surgical system 10. For example, one method of treating focal atrial fibrillation with the lesion formation apparatus 100 involves the creation of transmural lesions around the pulmonary veins. Lesions may be created around the pulmonary veins individually, in pairs, or, as is illustrated in FIG. 4A, a single transmural epicardial lesion L may be created around all four of the pulmonary veins PV. Such a lesion may be formed by positioning the lesion formation apparatus 100 around the pulmonary veins PV in the manner illustrated in FIG. 4. The connector device 106 may be used to secure the longitudinal ends of the inflatable cryogenic element 102 in close proximity to one another. Although there is a slight space between the ends of the inflatable cryogenic element 102 in FIG. 4 in order to more clearly show various elements of the illustrated embodiment, the ends would typically be in contact with one another or slightly overlap in actual use. Cryogenic fluid from the cryogenic fluid supply and control apparatus 200 is then passed through the inflatable cryogenic element 102, by way of the infusion and ventilation lumens 110 and 112, to form the lesion.

The inflatable cryogenic element 102 illustrated in FIGS. 1-3 is preferably formed from a thin tube 116. Referring more specifically to FIGS. 2 and 3, the tube 116 may be flattened against the base member 104 and secured to the base member with adhesive 118. Flattening the tube 116 and securing it to the base member 104 in this manner prevents the tube from buckling when pulled into a loop, increases the amount of surface area that will be in contact with tissue when the inflatable cryogenic element 102 is pressurized (or "inflated"), improves contact stability when the inflatable cryogenic element is pressurized, and minimizes folding and twisting of the cryogenic element when it is deflated. Flattening the tube 116 and securing it to the base member 104 in this manner also increases the strength of the bond between the tube and the base member and minimized the profile (i.e. the height in the orientation illustrated in FIGS. 1-3) of the lesion formation apparatus 100. Additionally, in those instances where the base member 104 is formed from insulating material (discussed below), this configuration insures that about one-half of the inflatable cryogenic element 102 will be thermally isolated from tissue.

The exemplary tube 116 is preferably formed from material that is relatively high in thermal conductivity. A suitable temperature gradient across the wall of the tube is about 2.degree. C. or less. The tube material should also result in an inflatable cryogenic element 102 that has a burst pressure rating which exceeds the operating pressures within the inflatable cryogenic element. In the illustrated implementations for example, and assuming that liquid perfluorocarbon will be supplied to the inflatable cryogenic element 102 at a rate of 300 ml/min. and a temperature of minus 100.degree. C., a suitable burst pressure rating would be about 760 mm Hg (1 atmosphere). Another important consideration is tear resistance because the inflatable cryogenic element 102 will be subjected to forces that could result in tearing (and leaks) when the lesion formation apparatus 100 is deployed around a body structure. For example, the inflatable cryogenic element 102 will be subjected to relatively large tearing forces when deployed around the inferior pulmonary veins in the posterior aspect to the heart. The present inventors have determined that inflatable cryogenic elements with a burst pressure rating of about 3800 mm Hg (5 atmospheres) will not tear under these conditions. Accordingly, a suitable burst pressure rating is about 3800 mm Hg (5 atmospheres).

In one mode of operation, the inflatable cryogenic element 102 may be supplied with liquid cooling fluid in such a manner that, as the liquid cooling fluid flows through the inflatable cryogenic element, the pressure within the cryogenic element will be less than about 100 mm Hg, which results in a resilient cryogenic element. Such a resilient cryogenic element is softer and less traumatic to tissue than turgid cryogenic elements (i.e. those whose internal pressure is greater than 100 mm Hg). It is also able to better conform to tissue. It should also be noted that there are a variety of ways to achieve the relatively low pressures (i.e. less than 100 mm Hg) within the inflatable cryogenic element 102. For example, configuring the infusion and ventilation lumens 110 and 112 such that the cross-sectional area of the infusion lumen is less than that of the ventilation lumen is one way to produce a low pressure within the inflatable cryogenic element 102.

Although the present inventions are not limited to any particular materials, suitable materials for the inflatable cryogenic element 102 include biaxially oriented polyethylene terephthalate (PET), Nylon, and Pebax® heat shrink tubing. The wall of such tubing will typically be about 0.001 inch to 0.0005 inch thick. Conductive polymer mixtures (such as 25% graphite filled Pebax® 2533), which allow for thicker walls while maintaining adequate levels of heat transfer, are other examples of suitable materials. Semi-compliant, compliant and elastomeric materials may also be employed. Here, thicknesses of about 0.004 inch to 0.008 inch would be required to compensate for stretching.

In addition to supporting the inflatable cryogenic element 102, the base member 104 in the illustrated embodiment functions as an insulation device to protect non-target tissue adjacent to the target tissue from the cryogenic element. The exemplary base member 104 is a flexible device that, as illustrated in FIGS. 2 and 3, is generally rectangular in cross-section. However, a wide variety of alternative configurations are possible. Such configurations include, but are not limited to, the configurations illustrated in FIGS. 5-8. Referring first to FIG. 5, the base member 104a includes a groove 120 which receives a portion of the cryogenic element 102. Such a configuration provides a relatively low profile, reduces the possibility that the cryogenic element will separate from the base member, provides additional lateral insulation, and reduces the likelihood that the cryogenic element will collapse. The exemplary base member 104b illustrated in FIG. 6 wraps around the sides of the cryogenic element 102 in order to prevent the ablation of tissue that is laterally adjacent to the target tissue. Alternatively, the sides of the base member may simply extend laterally beyond the sides of the cryogenic element 102. Turning to FIG. 7, the exemplary base member 104c is a composite formed from a number of layers of different materials. Such composites can be configured for superior twist resistance or pre-shaped to aid the physician during the positioning process.

The exemplary base member 104d illustrated in FIG. 8 includes a plurality of reinforcing members 122, such as straight or pre-shaped polymer, composite or metal members, that prevent twisting of the lesion formation apparatus 100, hold a shaped lesion formation apparatus straight for introduction, or provide lumens for temperature sensor wires or other elements. Alternatively, as illustrated in FIG. 8A, the exemplary base member 104e simply includes a plurality of lumens 123.

Base members may also perform specific functions within a lesion formation apparatus. As illustrated for example in FIGS. 8B-8D, a base member 104f in the lesion formation apparatus 100h includes a pre-shaped reinforcing member 122a (e.g. a thin strip of Nitinol) with a pre-shaped loop configuration and a removable stylet 122b (e.g. a steel rod) that is straight and rigid enough to overcome the bending forces applied by pre-shaped reinforcing member 122a. The removable stylet 122b is carried within a tube 122c that defines a longitudinally extending lumen within the base member 104f. Absent the presence of the removable stylet 122b, the base member 104f, with its pre-shaped reinforcing member 122a, will bend the lesion formation apparatus 100h into a loop and will maintain the loop during lesion formation procedures.

In the illustrated embodiment, the longitudinal ends of the cryogenic element 102 overlap slightly in order to insure that the lesion formed thereby will be a complete circle. Alternatively, pre-shaped reinforcing member 122a may be configured such that the longitudinal ends abut one another, or such that there is a gap between the longitudinal ends, if the intended application so requires. Additionally, although the illustrated reinforcing member has a substantially circular shape, any shape suitable for the intended application may be employed. Finally, a pre-shaped reinforcing member and stylet may be incorporated into any of the lesion formation apparatus described herein with reference to FIGS. 1-32.

During use, the removable stylet 122b will be in place within the tube 122c prior to deployment of the associated lesion formation apparatus. The removable stylet 122b will be withdrawn in the direction of arrow A as the apparatus is advanced in a direction tangential to the target tissue structure, thereby allowing the pre-shaped reinforcing member 122a to bend the apparatus into a loop shape around the target structure. The stylet 122b is preferably slightly longer than the base member 104f is order to provide a free end that may be grasped by the physician. The stylet 122b may, in some instances, have a slight curvature where applications so require.

In addition to bending the lesion formation apparatus 100h into the bent orientation illustrated in FIG. 8D, the pre-shaped reinforcing member 122a will maintain the lesion formation apparatus in the bent orientation during lesion formation procedures. As such, the connector device 106 need not be used (although it may be used if desired) to maintain the lesion formation apparatus in the loop orientation. The end portions 126 and 128 may still be used, however, to pull the lesion formation apparatus around a tissue structure as it is being positioned for a procedure.

In other alternative base member configurations, the cross-sectional shape (in the orientation illustrated in FIGS. 5-8) may be varied. For example, instead of the rectangular cross-sectional shape illustrated in FIGS. 1-3, the cross-sectional base members may be thicker, thinner, circular, semi-circular, triangular, or any other shape that is suitable for the intended use. Base members in accordance with the present inventions may also be hollow (e.g. molded hollow bodies) or have a plurality of small channels formed therein.

Although the present inventions are not limited to any particular materials, suitable materials for the base members 104-104d include flexible polymer (elastomer) open and closed cell foams. In those instance where open cell foams are used, the base member may include a sealing skin (not shown) to prevent fluid absorption. Flexible thermoplastics and thermoset polymers may also be employed. The base members are also preferably insulating and, in some instances, transfer heat at a rate of 0.33 w/cm.sup.2 of exposed surface area, which is low enough to prevent freezing. A typical thermal conductivity for an insulator is less than about 0.002 w/cm-K. Foams having a thickness of about 2 mm will provide this level of insulation, as will thin (e.g. 0.8 mm) balloons filed with a gas such as $CO_2$. In addition to protecting adjacent tissue from the extremely lower temperatures associated with the inflatable cryogenic element 102, an insulating base member makes the lesion formation apparatus "one directional" in that heat transfer to the cryogenic element will take place on the surface opposite the base member. Such an arrangement is more efficient that one in which the heat transfer can take place along the entire perimeter of the cryogenic element 102.

As illustrated in FIGS. 1-4, the exemplary connector device 106 is a relatively thin, flexible elongate device that includes a main portion 124 and a pair of end portions 126 and 128. The main portion 124 is secured to the base member 104, preferably along the entire length of the base member. The end portions 126 and 128, which extend from the longitudinal ends of base member 104, may be used to pull the lesion formation apparatus 100 into the orientation illustrated in FIG. 4 and then tied onto a knot 130 to hold the lesion formation apparatus in place. The end portions 126 and 128 may also be provided with knots, beads, eyelets and/or any other closure mechanism that can be used to hold the end portions (as well as the longitudinal ends of the inflatable cryogenic element 102 and base member 104) in the orientation illustrated in FIG. 4. It should be noted that the connector device 106 is preferably, although not necessarily, secured to the side of the base member 104 opposite the inflatable cryogenic element 102, as opposed to in between the base member and cryogenic element. Such an arrangement isolates the cryogenic element 102 from the pulling stresses associated with the introduction, positioning and securing of the lesion formation apparatus 100.

Although the present inventions are not limited to any particular materials, one suitable material for the connector device 106 is thin (e.g. about 0.005 inch to 0.025 inch) woven fabric ribbon. This material is relatively soft and will not slice through tissue during use. Other suitable materials include polymer films and cords. The main portion 124 may be secured to the base member 104 with a flexible adhesive (not shown) such as polyurethane or a Polycin® and Vorite® mixture.

The exemplary infusion and ventilation lumens 110 and 112 (FIGS. 1 and 3) will typically extend about 3 mm to 10 mm into the respective longitudinal ends of the inflatable cryogenic element 102 and are provided with polycarbonate Luer connectors 132 and 134 that may be used to connect the infusion and ventilation lumens to a source of cryogenic fluid by way of, for example, the tubes 210 and 212 (FIG. 4). Depending on the type of cryogenic cooling that is desired, the infusion and ventilation lumens may be used to supply and ventilate super-cooled fluid, such as liquid perfluorocarbon that has been cooled to a suitably low temperature such as minus 100.degree. C., or to supply liquid nitrous oxide and ventilate the gas that results from the expansion within the inflatable cryogenic element 102. Other suitable connectors include stopcocks, valves, check valves, T or Y-fittings adapted for purging/flushing or temperature monitoring. In order to withstand the extremely cold temperatures associated with cryogenic cooling, the infusion and ventilation lumens 110 and 112 are preferably formed from materials such as Tygon®, C-Flex®, or a polyurethane polymer. The infusion and ventilation lumens 110 and 112 may also be insulated for improved performance and safety.

As noted above, adhesive material 114 (FIG. 3) may be used to secure the infusion and ventilation lumens 110 and 112 in place, as well as to seal the longitudinal ends of the inflatable cryogenic element 102. Suitable adhesives include flexible UV activated adhesives such as Loctite® 3321 and 3021. Alternatively, the infusion and ventilation lumens 110 and 112 may be secured in place and the ends of the inflatable cryogenic element 102 sealed by heat curing or RTV polyurethane. The adhesive 118 is preferably a Vorite® and polycin polyurethane blend.

The overall dimensions of lesion formation apparatus in accordance with the present inventions will, of course, depend on the intended application. In one exemplary implementation that is suitable for forming epicardial lesions around the pulmonary veins, the inflatable cryogenic element 102 is about 15 cm to 30 cm in length. The aspect ratio, i.e. the width to thickness (or height) ratio, is about 2-3 to 1. Typically, in the orientation illustrated in FIG. 3, the width inflatable cryogenic element 102 is about 4 mm to 12 mm and the thickness is about 1 mm to 4 mm, when secured to the base member 104 in the manner illustrated in FIG. 3. The length and width of the base member 104 corresponds to that of the cryogenic element 102 in the exemplary implementation, i.e. the base member is about 15 cm to 30 cm in length and about 4 mm to 12 mm wide. The thickness, which depends on the materials, will typically be about 1 mm to 7 mm. With respect to the exemplary connector device 106, the width will correspond to that of the base member 104 and, accordingly, is about 4 mm to 12 mm. The end portions 126 and 128 extend about 15 cm to 60 cm from the longitudinal ends of the cryogenic element.

Another exemplary lesion formation apparatus is generally represented by reference numeral 100a in FIGS. 9-12. The lesion formation apparatus 100a is substantially similar to the lesion formation apparatus 100 described above with reference to FIGS. 1-8 and similar elements are represented by similar reference numerals. Here, however, the inflatable cryogenic element 102a includes a support structure 136. A variety of different support structures may be employed. In the illustrated embodiment, for example, the support structure is a spiral coil extends from a point slightly inside one longitudinal end of the inflatable cryogenic element 102a (i.e. about 1 mm to 4 mm) to a point slightly inside the other longitudinal end. The support structure 136, which includes short, linear longitudinal end portions 138 that are held in place by the adhesive 114, may be formed from a thin wire, such as a Nitinol wire that is about 0.016 inch in diameter. The overall diameter of the support structure 136 itself will depend on the intended application. In epicardial applications such as that illustrated in FIG. 4, the diameter will typically be about 2 mm to 4 mm. Aluminum, stainless steel, copper or silver wires may also be used in order to improve heat transfer from the tissue to the fluid. Thin layers of adhesive 114 are also deposited within the lateral edges of the tube 116 in order to prevent draping or bagging.

There are a number of advantages associated with the use of a support structure such as the support structure 136. For example, the support structure insures that the fluid transmission space 108 will have a substantially constant cross-sectional area. A coil-type support structure (e.g. the support structure 136) will also create secondary flow within the transmission space, which increases thermal efficiency. Coil-type support structures also create ridges that may help the associated lesion formation apparatus engage soft or fatty substrates for thermal transmission, provide anchoring stability and increase contact surface area.

Another exemplary lesion formation apparatus is generally represented by reference numeral 100b in FIGS. 13-16. The lesion formation apparatus 100b is substantially similar to the lesion formation apparatus 100a described above with reference to FIGS. 9-12 and similar elements are represented by similar reference numerals. Here, however, the inflatable cryogenic element 102b has a relatively non-compliant inner region and a relatively compliant outer region. The relatively compliant outer region allows the lesion formation apparatus 100b to conform to tissue, thereby insuring good tissue contact, and also acts a barrier in the event of any leakage from the inner region.

In the exemplary implementation illustrated in FIGS. 13-16, the outer region of the inflatable cryogenic element 102b includes an outer fluid transmission space 109 that is defined by a thin outer tube 117, while the inner region includes an inner fluid transmission space 108 that is defined by a thin inner tube 116b located within the outer tube. The outer fluid transmission space 109 is connected to a source of thermally conductive media by infusion and ventilation lumens 111 and 113, and the inner fluid transmission space 108 is connected to a source of cryogenic fluid by the infusion and ventilation lumens 110 and 112. The shape of the inner fluid transmission space 108 is generally maintained by the support structure 136, which also prevents the outer tube 117 from occluding the inner tube 116b.

The outer tube 117 is preferably formed from thin (e.g. about 0.002 inch), compliant (or elastomeric) and thermally conductive material such as unrecovered PET or polyurethane rubber. The longitudinal ends of the outer tube 117 are sealed around the inner tube 116b and the infusion and ventilation lumens 111 and 113 with adhesive 114. The outer tube 116b is flattened against the base member 104 and secured to the base member with adhesive 118. The inner tube 116b may be formed from a relatively non-complaint material, such as recovered PET, that is heat shrunk onto the support structure 136. Adhesive 114 is also used to seal the longitudinal ends of the inner tube 116b around the infusion and ventilation lumens 110 and 112. Stopcocks 133 and 133 are provided on the inlet lumens 110 and 111, and stopcocks 135 and 135 are provided on the outlet lumens 112 and 113. The stopcocks may be used to exclude air bubbles from purged, filled spaces and to prevent fluid leakage during removal of the apparatus from the patient and to maintain the inflated geometry after the cryogenic supply and control apparatus 200 has stopped supplying fluid. It should also be noted that stopcocks 133 and 135 may be used in place of the Luer connectors 132 and 134 in the other embodiments disclosed herein.

Prior to use, the outer fluid transmission space 109 will be purged of air. After the lesion formation apparatus 100b is positioned adjacent to the target tissue (e.g. in the manner illustrated in FIG. 4), the fluid transmission space 109 will be filled with a thermally conductive media such as water. Cryogenic fluid is then directed through the inner fluid transmission space 108. In those instances where the outer fluid transmission space is filled with water, the water will typically turn to ice. Heat is then transferred from the tissue, through the outer tube 117, the conductive media therein, and the inner tube 116b to the cryogenic fluid.

Another exemplary lesion formation apparatus is generally represented by reference numeral 100c in FIGS. 17-20. The lesion formation apparatus 100c is substantially similar to the lesion formation apparatus 100 described above with reference to FIGS. 1-8 and similar elements are represented by similar reference numerals. Here, however, the infusion and ventilation lumens 110 and 112 extend from the same longitudinal end of the lesion formation apparatus. The inlet lumen 110 extends a short distance into the inflatable cryogenic element 102 and is held in place with adhesive material 114. The adhesive material 114 also seals that longitudinal end of the inflatable cryogenic element 102. A portion of the outlet lumen 112 extends under the cryogenic element 102 to a point beyond the other longitudinal end of the cryogenic element. An end cap 140, which is associated with the other end of the cryogenic element 102, transfers the cryogenic fluid from the cryogenic element to the outlet lumen 112.

In the exemplary implementation illustrated in FIGS. 17-20, a short connector lumen 112c extends from the end of the inflatable cryogenic element into the end cap 140. The lumen 112c is held in place with adhesive material 114, which also seals that longitudinal end of the inflatable cryogenic element 102. The end cap 140 includes a base portion 142 and a cover 144 that define an inner region 146 which is open at both ends. The end cap may, alternatively, be a one piece design. The connector lumen 112c and outlet lumen 112 extend into one end of the inner region 146, which is sealed with the adhesive 114. The other end of the inner region 146 is also sealed with adhesive 114. Cryogenic fluid that exits the cryogenic element 102 by way of the connector lumen 112c flows though a space 150 within the end cap 140 (i.e. the portion of the inner region 146 between the adhesive material) and into the outlet lumen 112. The cryogenic fluid then passes under the cryogenic element 102 on its way out of the lesion formation apparatus 100c.

It should be noted that the concept of placing infusion and ventilation lumens at one end of an inflatable cryogenic element, and an end cap (or end caps) at the other end, is also applicable to the exemplary apparatus 100a illustrated in FIGS. 9-12 and the exemplary apparatus 100b illustrated in FIGS. 13-16.

As illustrated above, the configurations of the inflatable cryogenic element and base member are susceptible to a wide degree of variation. There are also a number of alternative connector configurations. Turning to FIGS. 21-24, the exemplary lesion formation apparatus 100d is substantially similar to the lesion formation apparatus 100 described above with reference to FIGS. 1-8 and similar elements are represented by similar reference numerals. Here, however, the lesion formation apparatus 100d includes a fastener 148 that may be used instead of, or in addition to, the connector device 106 when fixing the position of the apparatus around an organ.

In the exemplary implementation illustrated in FIGS. 21-24, the fastener 148 includes a pair of fastening elements 150 and 152 that are associated with the longitudinal ends of the inflatable cryogenic element 102. The exemplary fastening elements 150 and 152 are hook and loop fastener strips, such as Velcro® strips. Fastening element 150 is carried on the bottom of the connector device main portion 124 and faces downwardly (in the orientation illustrated in FIG. 21), while the fastening element 152 is carried by a support 154 that is secured to the connector device main portion and faces upwardly. So arranged, the fastening elements 150 and 152 will face one another, thereby allowing them to be connected to one another, when the lesion formation apparatus 100d is bent into a loop in the manner illustrated in FIG. 24.

Other exemplary fastening elements include devices that will hold the connector device end portions 126 and 128, such as clamps and spring-biased locks. In those instances where the end portions 126 and 128 include knots, cleats (i.e. a tube with slots that receive the knots) may be employed.

The exemplary fastener 148 may also be used in combination with the lesion formation apparatus 100a illustrated in FIGS. 9-12, the exemplary lesion formation apparatus 100b illustrated in FIGS. 13-16, and the exemplary lesion formation apparatus 100c illustrated in FIGS. 17-20.

Another exemplary lesion formation apparatus is generally represented by reference numeral 100e in FIGS. 25 and 26. The lesion formation apparatus 100e is substantially similar to the lesion formation apparatus 100 described above with reference to FIGS. 1-8 and similar elements are represented by similar reference numerals. Here, however, the connector device 106e includes a pair of flexible pull strings 124e and 125e and a pair of flexible end strings 126e and 128e. The pull strings 124e and 125e are secured to the base member 104, and preferably along the entire length of the base member, with adhesive 118. The longitudinal ends of the pull strings 124e and 125e are secured to one another, and to the end strings 126e and 128e, by knots 127e (or other fastening methods). The connector device 106e may also be used in place of the connector device 106 in the lesion formation apparatus 100a-d illustrated in FIGS. 9-24.

The exemplary lesion formation apparatus illustrated in FIGS. 1-26 may also be configured in a manner that will help the physician distinguish various elements from one another. For example, the lesion formation apparatus 100f illustrated in FIG. 27, which is essentially identical to the apparatus 100 described above with reference to FIGS. 1-8, includes a connector device 106f that is relatively dark in color, while the inflatable cryogenic element 102 is relatively light in color. This may also be reversed, with the cryogenic element 102 formed from a relatively dark material and the connector device 106f formed from a relatively light material. The color of the base member 104 may also be selected so as to help the physician identify various apparatus elements during surgical procedures. Stripes and other patterns may also be employed. A visible scale may also be provided on the cryogenic element, the base member or the connector device in order to allow the physician to monitor and manage the full length of the apparatus during the procedure.

The exemplary lesion formation apparatus illustrated in FIGS. 1-27 may also be provided with a movable insulation device that prevents some of the tissue that would otherwise be ablated by the inflatable cryogenic element from being ablated. As illustrated for example in FIGS. 28 and 29, a slidable insulation sleeve 156 is positioned around a portion of the lesion formation apparatus 100. The length of the insulation sleeve 156 will vary from application to application, but will typically be longer that the cryogenic element 102 itself and up to twice the length of the cryogenic element. This allows the insulation sleeve 156 to provide an insulative barrier between the lesion formation apparatus 100 and the patient, from the exterior of the body to the target tissue region. Suitable materials include polyurethane or silicone, and lumens 157 may be provided to increase the insulative capability of the sleeve. The insulation sleeve 156 may, for example, be used to cover the majority of the cryogenic element 102 during touch up procedures to fill in gaps in lesions. Here, the insulation sleeve 156 may be pulled proximally until the desired length of the cryogenic element 102 is exposed.

In an alternative configuration, which is illustrated in FIGS. 29A and 29B, the exemplary insulation sleeve 156a includes a window 159 that allows small lesions to be formed in specific locations. Sleeve 156a is also configured to prevent the lesion formation apparatus 100 from rotating and to insure that the inflatable cryogenic element 102 is aligned with the window 159. More specifically, the internal lumen of the insulation sleeve 156a is substantially D-shaped and the flat portion of the "D" is adjacent to the base member 104.

The exemplary lesion formation apparatus illustrated in FIGS. 1-29B may also be provided with one or more temperature sensors, such as thermocouples or thermistors, so that tissue temperature can be monitored during lesion formation procedures. Referring to FIGS. 30 and 31, the exemplary lesion formation apparatus 100g, which is substantially similar to the lesion formation apparatus 100 described above with reference to FIGS. 1-8, is provided with a plurality of temperature sensors 158. The temperature sensors 158 may be equally spaced along the length of the inflatable cryogenic element 102. In one exemplary implementation where the cryogenic element is 30 cm in length, the temperature sensors 158 are positioned such that adjacent temperature sensors are 5 cm apart and the two temperature sensors closest to the longitudinal ends of the cryogenic element are 5 cm from the longitudinal ends. The temperature sensors 158 may be secured to the inflatable cryogenic element 102 near the base member 104 with, for example, flexible UV activated adhesive 160.

Each temperature sensor 158 is connected to a signal wire 162 that transmits temperature information from the temperature sensors to, for example, the cryogenic fluid supply and control apparatus 200 (FIG. 4). The signal wires are secured to the inflatable cryogenic element 102 near the temperature sensors 158 with quick curing adhesive 164, such as cyanoacrylate, and are routed through a small diameter flexible polymer tube 165. The tube 165 is attached to the base member 104 adjacent to the inflatable cryogenic element 102. In the exemplary implementation illustrated in FIGS. 30 and 31, the signal wires 162 pass from the small diameter tube 165 and into a more robust tube (or cable) 166 at one end of the apparatus, and are then connected to an electrical connector 168. The connector 168 may, in turn, be connected to the cryogenic fluid supply and control apparatus 200.

The temperature sensor locations are not limited to those illustrated in FIGS. 30 and 31. For example, temperature sensors may be placed on both sides of the inflatable cryogenic element 102. Temperature sensors may, alternatively or in addition, also be placed along the top of the cryogenic element 102.

The exemplary lesion formation apparatus illustrated in FIGS. 1-29 may also be configured in such a manner that the number of uses is limited. Referring to FIG. 30, a valve 170 may be placed within an inflatable cryogenic element (e.g. the cryogenic element 102) that will, when closed, prevent the flow of cryogenic fluid from the fluid transmission space 108 to the ventilation lumen 112. Suitable valves include, but are not limited to, normally closed electronic-operating valves and normally closed solenoid valves. The valve 170 may be connected to the connector 168 for control purposes (as shown) or have its own connector. The exemplary valve 170 also includes a battery and a timer circuit (not shown).

Regardless of the type of valve used, the valve 170 will be opened the first time that the connector 168 is connected to the cryogenic fluid supply and control apparatus 200. When connected, the valve will open, battery will be charged and the timer circuit will begin tracking time. After a predetermined period (e.g. 24 hrs.), the valve 170 will close permanently, thereby preventing further use.

It should be noted that the exemplary valve 170 need not be located within the inflatable cryogenic element. As illustrated in FIG. 32, for example, the valve 170 may be located along a portion of the ventilation lumen 112. Alternatively, the valve may be located along a portion of the inlet lumen 110.

III. Exemplary Clamp Based Lesion Formation Apparatus

Figure 33:
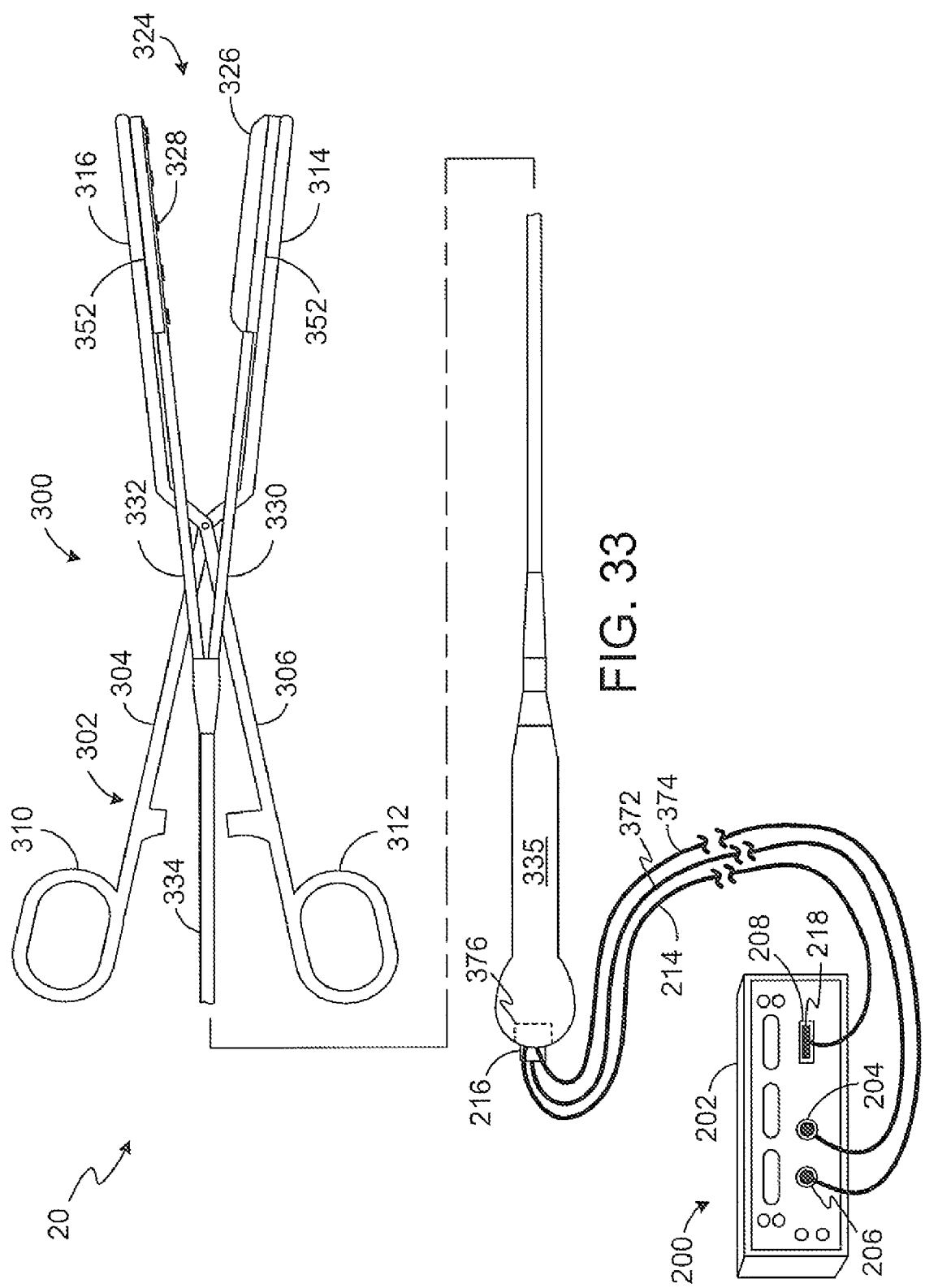
FIG. 33 is a perspective view of a surgical system in accordance with a preferred embodiment of a present invention.

As illustrated for example in FIG. 33, an exemplary surgical system 20 in accordance with one embodiment of a present invention includes the cryogenic fluid supply and control apparatus 200 and a cryogenic clamp apparatus 300. The cryogenic clamp apparatus 300 includes a clamp and a tissue coagulation assembly that may be secured to the clamp. As used herein, the term "clamp" includes, but is not limited to, clamps, clips, forceps, hemostats, and any other surgical device that includes a pair of opposable clamp members that hold tissue, at least one of which is movable relative to the other. In some instances, the clamp members are connected to a scissors-like arrangement including a pair of handle supporting arms that are pivotably connected to one another. The clamp members are secured to one end of the arms and the handles are secured to the other end. Certain clamps that are particularly useful in minimally invasive procedures also include a pair of handles and a pair of clamp members. Here, however, the clamp members and handles are not mounted on the opposite ends of the same arm. Instead, the handles are carried by one end of an elongate housing and the clamp members are carried by the other. A suitable mechanical linkage located within the housing causes the clamp members to move relative to one another in response to movement of the handles. The clamp members may be linear or have a predefined curvature that is optimized for a particular surgical procedure or portion thereof. The clamp members may also be rigid or malleable.

Figure 42:
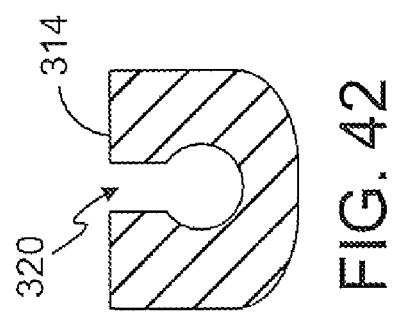
FIG. 42 is a section view taken along line 42-42 in FIG. 41.
Figure 41:
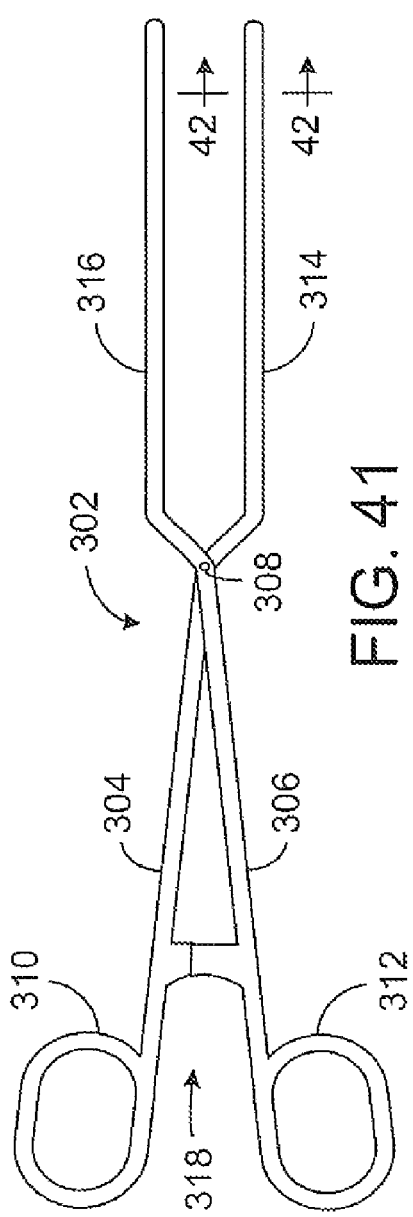
FIG. 41 is a plan view of a clamp in accordance with a preferred embodiment of a present invention.
Figure 43:
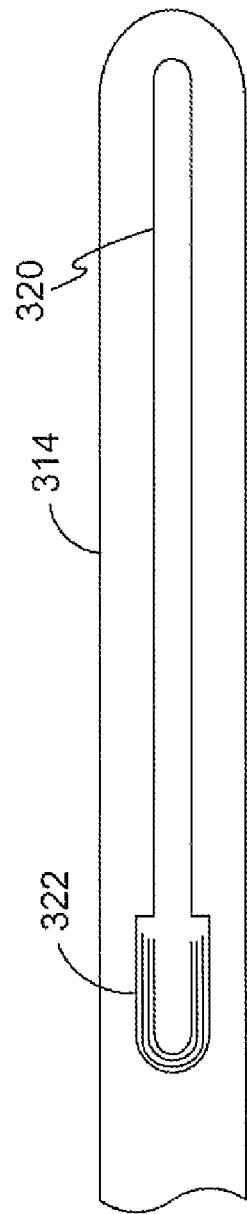
FIG. 43 is a top view of a portion of the clamp illustrated in FIG. 41.

One example of a clamp that may be employed in the cryogenic clamp apparatus 300 is generally represented by reference numeral 302 in FIGS. 33 and 41-43. Referring more specifically to FIGS. 41-43, the clamp 302 includes a pair of rigid arms 304 and 306 that are pivotably connected to one another by a pin 308. The proximal ends of the arms 304 and 306 are respectively connected to a pair handle members 310 and 312, while the distal ends are respectively connected to a pair of clamp members 314 and 316. The clamp members 314 and 316 may be rigid or malleable and, if rigid, may be linear or have a pre-shaped curvature. A locking device 318 locks the clamp in the closed orientation, and prevents the clamp members 314 and 316 from coming any closer to one another than is illustrated in FIG. 41, thereby defining a predetermined spacing between the clamp members. The clamp 302 is also configured for use with a pair of soft, deformable inserts (not shown) that may be removably carried by the clamp members 314 and 316 and allow the clamp to firmly grip a bodily structure without damaging the structure. To that end, the clamp members 314 and 316 each include a slot 320 (FIGS. 42 and 43) that is provided with a sloped inlet area 322 and the inserts include mating structures that are removably friction fit within the slots. The exemplary tissue coagulation assembly 324 (FIGS. 33 and 34) may be mounted on the clamp members in place of the inserts.

As illustrated in FIGS. 33-37, the exemplary tissue coagulation assembly 324, includes an inflatable cryogenic element 326 and a series of temperature sensors 328, such as thermocouples or thermistors. The inflatable cryogenic element 326 and temperature sensors 328 are respectively carried on support structures 330 and 332, which are connected to a tubular member 334 by a connector 336. The tubular member 334 is secured to a handle 335. The inflatable cryogenic element 326 may be connected to a source of cryogenic fluid, such as the cryogenic fluid supply and control apparatus 200 and, to that end, the support structure 330 includes an infusion lumen 338 and a ventilation lumen 340. The temperature sensors 328 are connected to signal wires 342 which pass through a signal wire lumen 344 in the support structure 332. The tubular member 334 includes infusion and ventilation lumens 346 and 348 and a signal wire lumen 350, which are respectively connected to the infusion and ventilation lumens 338 and 340 in the support structure 330, and the signal wire lumen 344 in the support structure 332, by the connector 336.

The exemplary tissue coagulation assembly 324 also includes a pair of essentially identical base members 352 which are used to connect the assembly to the clamp 502. Although the configuration of the tissue coagulation assembly may vary from application to application to suit particular situations, the exemplary tissue coagulation assembly 324 is configured such that the inflatable cryogenic element 326 and the temperature sensors 328 will be parallel to one another as well as relatively close to one another (i.e. a spacing of about 1-10 mm) when the clamp 502 is in the closed orientation. Such an arrangement will allow the tissue coagulation assembly to firmly grip a bodily structure without cutting through the structure. Referring more specifically to FIGS. 38-40A, the illustrated base members 352 include a main portion 354, with a groove 356 that is configured to receive the support structure 330 (or 332), and a connector 358 that is configured to removably mate with the slot 320 in the clamp 302. The configuration of the groove 356 allows the support structure 330 (or 332) to be snap fit into the base member 352. Adhesive may also be used within the groove 356 to insure that the inflatable cryogenic element 326 and support structure 332 do not separate from the base members 352. The exemplary connector 358 is provided with a relatively thin portion 360 and a relatively wide portion 362, which may consist of a plurality of spaced members (as shown) or an elongate unitary structure, in order to correspond to the shape of the slot 320 in the clamp 302.

The exemplary inflatable cryogenic element 326 is formed from a thin, flexible tube 364 (FIGS. 39 and 40) that is positioned around the support structure 330. A small portion of the tube 364 is wedged between the outer surface of the support structure 330 and the groove 356 in the base member 352, while the remainder of the tube bulges out and, when inflated, defines the fluid transmission space 366. To that end, the support structure 330 includes an infusion aperture 368 that connects the infusion lumen 338 to the fluid transmission space 366, and a ventilation aperture 370 that connects the fluid transmission space to the ventilation lumen 340. The infusion aperture 368 is preferably (although not necessarily) located near the distal end of the inflatable cryogenic element 326 and the ventilation aperture 370 is located near the proximal end. The longitudinal ends of the tube 364 are sealed around the support structure 330 with adhesive 371 (FIG. 40A). Suitable adhesives include UV activated adhesives and cyanoacrylate.

The exemplary inflatable cryogenic element 326 is preferably wider than it is tall in order to increase the surface area that will be in contact with tissue during use. In the exemplary implementation illustrated in FIGS. 38-40, the portion of the tube 364 that is above the base member 352 is generally elliptical in shape, thereby defining a generally elliptical inflatable cryogenic element 326 (note the cross-sectional shape illustrated in FIGS. 39 and 40). The major axis (i.e. width) to minor axis (i.e. height) ratio is about 2 to 1 in the exemplary embodiment, e.g. a major axis of about 4 mm and a minor axis of about 2 mm in epicardial applications. Of course, the cross-section shape may be varied from application to application. The length of the inflatable cryogenic element 326 will also vary from application to application and may be about 5 cm to 8 cm in epicardial applications.

With respect to materials, the inflatable cryogenic element 326 is preferably formed from the same materials as the inflatable cryogenic element 102. However, because the inflatable cryogenic element 326 is being used in combination with a clamp, it will not be subjected to the same shear (or "tearing") stresses that the inflatable cryogenic element 102. As a result, the inflatable cryogenic element 326 may be configured with a lower burst pressure rating, e.g. about 760 mm Hg (1 atmosphere), which allows the material to be of lower ultimate strength. As the liquid cooling fluid flows through the inflatable cryogenic element 326, the pressure within the inflatable cryogenic element will typically be less than about 100 mm Hg, which results in a resilient cryogenic element. Such a resilient cryogenic element is softer and less traumatic to tissue than turgid cryogenic elements (i.e. those whose internal pressure is greater than 100 mm Hg). It is also able to better conform to tissue. Conventional cryogenic elements that employ the JT effect operate with internal gas pressures on the order of 700 mm Hg and are quite turgid.

It should be noted here that there are a variety of ways to achieve the relatively low pressures (i.e. less than 100 mm Hg) within the inflatable cryogenic element 326. For example, the support structure 330 may be configured such that the cross-sectional area of the infusion lumen 338 is less than that of the ventilation lumen 340.

Turning to the material used to form the other elements, the support structures 330 and 332 and tubular member 334 may be formed from PET or polyurethane tubing. The base members 352 may be formed from polyurethane, nylon, Pebax®, silicone, ceramics or metals such as aluminum, copper, stainless steel and Nitinol.

Referring to FIG. 33, the tissue coagulation assembly 324 may be connected to, for example, the cryogenic fluid supply and control apparatus 200 by way of fluid inlet and outlet tubes 372 and 374. The fluid inlet and outlet tubes 372 and 374, which extend through the handle 335 and are connected to the infusion and ventilation lumens 346 and 348 in the tubular member 334, may be connected to the fluid ports 204 and 206 on the cryogenic fluid supply and control apparatus 200. The signal wires 342 also extend through the handle 335 and terminate at an electrical connector 376. A cable 214, with electrical connectors 216 and 218, may be used to electrically connect the temperature sensors on the tissue coagulation assembly 324 to the electrical connector 208 on the cryogenic fluid supply and control apparatus 200.

The exemplary cryogenic clamp apparatus 300 may be reconfigured in a variety of ways. By way of example, but not limitation, one alternative tissue coagulation assembly includes a pair of the inflatable cryogenic elements 326. Each of the support structures carry an inflatable cryogenic element 326 and are configured in a manner similar to the support structure 330. Here, temperature sensors may be provided on one or both of the inflatable cryogenic elements 326. The tissue coagulation assembly 324 may also be provided with apparatus, such as the valve 170 illustrated in FIG. 30, to prevent multiple uses. Additionally, should applications so require, any of the features of the inflatable cryogenic elements discussed in Section II (e.g. the support structure 136 or the outer fluid transmission space 109) may be incorporated into the inflatable cryogenic elements 326.

The exemplary cryogenic clamp apparatus 300 may be used to form lesions in the following manner. The clamp members 314 and 316 may be positioned such that the inflatable cryogenic element 326 (in a deflated state) and the temperature sensors 328 are on opposite sides of a tissue structure. For example, the inflatable cryogenic element 326 and temperature sensors 328 may be positioned on opposites side of a single pulmonary vein or a pair of pulmonary veins. The clamp members 314 and 316 may then be brought into a completely closed orientation or, depending on the tissue structure, a slightly open orientation so long as the tissue structure is firmly held. Cryogenic liquid is then pumped from the cryogenic fluid supply and control apparatus 200 into the inflatable cryogenic element 326, thereby inflating the cryogenic element and cooling the target tissue. The temperature sensors 328 monitor the tissue temperature on the side of the target tissue structure opposite the inflatable cryogenic element 326.

The inventors herein have determine that temperature on the side of the target tissue structure opposite the inflatable cryogenic element 326 is indicative of lesion transmurality (i.e. whether or not a lesion that extends from one side of the target tissue structure to the other has been formed). More specifically, the inventors herein have determined that measured temperatures of about minus 20.degree. C. to about minus 40.degree. C. on the side of the tissue structure opposite the side that is in contact with the inflatable cryogenic element 326 are indicative of the formation of a transmural lesion. The cryogenic fluid supply and control apparatus 200 may, therefore, be configured to discontinue the flow of cryogenic liquid to the inflatable cryogenic element 326 when a predetermined temperature (e.g. a temperature between about minus 20.degree. C. and about minus 40.degree. C.) is measured by the temperature sensors 328. Alternatively, or in addition, the cryogenic fluid supply and control apparatus 200 may also be configured to provide an audible or visible indication that the predetermined temperature has been measured.

IV. Exemplary Probe Based Lesion Formation Apparatus

As illustrated for example in FIG. 44, an exemplary surgical system 30 in accordance with one embodiment of a present invention includes the cryogenic fluid supply and control apparatus 200 and a cryogenic surgical probe 400. Referring to FIGS. 44-50, the exemplary surgical probe 400 includes a relatively short shaft 402 and an inflatable cryogenic element 404 carried on the distal portion 406 of the shaft. The proximal portion 408 of the shaft 402 is secured to a handle 410. A strain relief element 412 is also provided. The shaft 402 will typically be about 3 cm to about 12 cm in length and will also typically be relatively stiff. In other words, the shaft is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial. The proximal portion 408 of the exemplary shaft 402 (FIG. 45) is malleable and consists of a malleable hypotube 414 with an outer polymer jacket 416. The distal portion 406 of the exemplary shaft 402 (FIG. 46) is malleable and consists of a malleable mandrel 418 and a support structure 420. The proximal end of the mandrel 418 is secured to the inner surface of the distal end of the hypotube 414 and the distal end of the mandrel is secured to a tip member 422. The tip member 422 is, in turn, secured to the distal end of the support structure 420 through the use of adhesive or other suitable instrumentalities.

As illustrated for example in FIGS. 44-46, the exemplary support structure 420 is a multi-lumen structure that includes an infusion lumen 424, a ventilation lumen 426, a signal wire lumen 428 and a center lumen 430 for the malleable mandrel 418. The distal ends of the infusion, ventilation, and signal wire lumens 424-428 are sealed by the tip member 422 and associated adhesive. The infusion and ventilation lumens 424 and 426 are respectively connected to infusion and ventilation tubes 432 and 434, which extend through the shaft proximal portion 408 and the handle 410 and may be connected to the fluid outlet and inlet ports 204 and 206 on the cryogenic fluid supply and control apparatus 200.

Referring to FIGS. 46-48, the exemplary inflatable cryogenic element 404 is formed from thin, flexible tube 436 that is positioned around the support structure 420. The proximal and distal ends of the tube 436 are secured to the support structure 420 with adhesive 438, such as UV activated adhesives or cyanoacrylate. When inflated, the inflatable cryogenic element 404 defines a fluid transmission space 440 between the inner surface of the tube 436 and the outer surface of the support structure 420. The adhesive 438 also seals the ends of the fluid transmission space 440. Additionally, the support structure 420 includes an infusion aperture 442 that connects the infusion lumen 424 to the fluid transmission space 440, and a ventilation aperture 444 that connects the fluid transmission space to the ventilation lumen 426. The infusion aperture 442 is preferably (although not necessarily) located near the distal end of the inflatable cryogenic element 404 and the ventilation aperture 444 is located near the proximal end.

With respect to materials and dimensions, the inflatable cryogenic element 404 is preferably formed from the same materials as the inflatable cryogenic element 102. However, because the inflatable cryogenic element 404 is being used in combination with a surgical probe, it will not be subjected to the same shear (or "tearing") stresses that the inflatable cryogenic element 102. As a result, the inflatable cryogenic element 404 may be configured with a lower burst pressure rating, e.g. about 760 mm Hg (1 atmosphere), which allows the material to be of lower ultimate strength. As the liquid cooling fluid flows through the inflatable cryogenic element 404, the pressure within the inflatable cryogenic element will typically be less than about 100 mm Hg, which results in a resilient cryogenic element. Such a resilient cryogenic element is softer and less traumatic to tissue than turgid cryogenic elements (i.e. those whose internal pressure is greater than 100 mm Hg). It is also able to better conform to tissue. The outer diameter of the cryogenic element 404 is about 4 mm to 6 mm in epicardial applications, while the length of the cryogenic element is about 3 cm to 12 cm and the outer diameter of the support structure 420 is about 2 mm to 3 mm.

It should be noted here that there are a variety of ways to achieve the relatively low pressures (i.e. less than 100 mm Hg) within the inflatable cryogenic element 404. For example, the support structure 420 may be configured such that the cross-sectional area of the infusion lumen 424 is less than that of the ventilation lumen 426.

The exemplary cryogenic surgical probe 400 illustrated in FIGS. 44-50 also includes a plurality of temperature sensors, such as thermocouples or thermistors. Referring more specifically to FIGS. 44 and 49, the exemplary implementation includes a first set of temperature sensors 446 on the outer surface of one side of the inflatable cryogenic element 404 and second set of temperature sensors 448 on the outer surface of the opposite side of the inflatable cryogenic element. Positioning temperature sensors on the outer surface of the inflatable cryogenic element 404 provides more accurate tissue temperature measurement that inner surface positioning. In the exemplary implementation, the temperature sensors in each set are arranged in a line, and the sets are about 180 degrees apart.

The temperature sensors 446 and 448 are connected to signal wires 450 which enter the signal wire lumen 428 by way of a series of signal wire apertures 452 on one side of the support structure 420. In the exemplary implementation, there are five (5) temperature sensors in each of the sets 446 and 448 and five (5) signal wire apertures 452 along one side of the support structure 420. As all of the signal wires 450 enter the signal wire lumen 428 on the same side of the support structure 420, the signal wires 450 associated with the temperature sensors 448 wrap around the support structure on their way to the associated signal wire apertures 452. Additionally, because some of the cryogenic fluid may leak into the signal wire lumen 428 through the signal wire apertures 452, the proximal end of the signal wire lumen is sealed with adhesive 454 (FIG. 50). The adhesive fills in any gaps between the signal wires 450 as well as any gaps between the signals wire and the inner surface of the signal wire lumen 428.

Proximal of the adhesive 454, the signal wire are twisted together and extend to a connector 456 in the handle 410. An electrical connection between the handle connector 456 and the cryogenic fluid supply and control apparatus 200 with the aforementioned cable 214.

The exemplary cryogenic surgical probe 400 may be reconfigured in a variety of ways. By way of example, but not limitation, in one alternative surgical probe, the ventilation lumen 426 and ventilation tube 434 are eliminated and the outlet aperture 442 is positioned near the center of the inflatable cryogenic element 404. An exterior ventilation lumen similar to the ventilation lumen 112 (FIG. 1) that extends a short distance into the longitudinal end of the cryogenic element 404 may be provided to ventilate the cryogenic fluid. Cryogenic surgical probes in accordance with the present inventions may also be provide with an insulative backing over a portion of the inflatable cryogenic element 404 in order to protect non-target tissue and increase the efficiency of the probe. Such an insulative backing could, for example, cover one-half of the surface area of the cryogenic element 404. Here, one of the temperature sensor sets may be eliminated. Additionally, should applications so require, any of the features of the inflatable cryogenic elements discussed in Section II (e.g. the support structure 136 or the outer fluid transmission space 109) may be incorporated into the inflatable cryogenic elements 404.

Although the inventions disclosed herein have been described in terms of the preferred embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims set forth below.

We claim:

1. A method of forming a lesion in tissue, the method comprising:
   positioning an apparatus including an inflatable cryogenic element in a looped orientation around a tissue structure;
   securing at least two portions of the apparatus relative to one another to maintain the looped orientation by tying the at least two portions together into a knot; and
   directing cryogenic fluid through the inflatable cryogenic element.

2. A method as claimed in claim 1, wherein the apparatus is positioned in the looped orientation around the tissue structure such that the inflatable cryogenic element is in contact with target tissue, and an insulation element is between the inflatable cryogenic element and non-target tissue.

3. A method as claimed in claim 1, the inflatable cryogenic element including first and second longitudinal end portions, wherein cryogenic fluid is directed into the first longitudinal end portion, through the inflatable cryogenic element, and out of the second longitudinal end portion.

4. A method as claimed in claim 1, wherein super-cooled liquid is directed through the inflatable cryogenic element.

5. A method as claimed in claim 1, the inflatable cryogenic element being positioned in the looped orientation around a pulmonary vein.

6. The method of claim 1, the apparatus comprising a main portion and first and second flexible end portions extending from opposite ends of the main portion, the first and second flexible end portions being pulled to position the apparatus into the looped orientation around the tissue structure.

7. The method of claim 6, the first and second end portions comprising respective first and second closure mechanisms to hold the first and second end portions and maintain the apparatus in the looped orientation.

8. The method of claim 7, the first and second end portions having first and second closure mechanisms comprising a bead or an eyelet.

9. The method of claim 7, the first and second end portions being tied together into the knot.

10. The method of claim 1, the apparatus positioned in the looped orientation comprising a woven fabric ribbon having a thickness of about 0.005 inch to about 0.025 inch.

11. The method of claim 1, the apparatus positioned in the looped orientation comprising a polymer.

* * * * *